(12) United States Patent
Pawlak et al.

(10) Patent No.: US 7,645,612 B2
(45) Date of Patent: Jan. 12, 2010

(54) KIT AND METHOD FOR MULTI-ANALYTE DETERMINATION

(75) Inventors: Michael Pawlak, Laufenburg (DE); Eginhard Schick, Rheinfelden (DE); Andreas Peter Abel, Basel (CH); Gert Ludwig Duveneck, Bad Krozingen (DE); Markus Ehrat, Magden (CH); Gerhard Matthias Kresbach, Staufen (DE); Eveline Schürmann-Mader, Zeihen (CH); Martin Andreas Bopp, Basel (CH)

(73) Assignee: Bayer Technology Services GmbH, Leverkusen (DE)

( * ) Notice: Subject to any disclaimer, the term of this patent is extended or adjusted under 35 U.S.C. 154(b) by 0 days.

(21) Appl. No.: 12/062,820

(22) Filed: Apr. 4, 2008

(65) Prior Publication Data

US 2008/0212070 A1  Sep. 4, 2008

Related U.S. Application Data

(62) Division of application No. 10/296,851, filed as application No. PCT/EP01/05995 on May 25, 2001, now Pat. No. 7,396,675.

(30) Foreign Application Priority Data

Jun. 2, 2000 (CH) .................................. 1104/00

(51) Int. Cl.
G01N 33/543 (2006.01)

(52) U.S. Cl. .................... 436/164; 422/50; 422/55; 422/82.05; 422/82.11; 435/287.2; 435/287.9; 435/288.7; 435/808; 435/975; 436/172; 436/518; 436/524; 436/525; 436/805; 436/808

(58) Field of Classification Search .................. 422/50, 422/55, 57, 82.05, 82.11; 435/287.2, 287.9, 435/288.7, 808, 975; 436/164, 172, 518, 436/524, 525, 805, 808
See application file for complete search history.

(56) References Cited

U.S. PATENT DOCUMENTS

| | | | |
|---|---|---|---|
| 4,815,843 A * | 3/1989 | Tiefenthaler et al. ........ 356/128 |
| 5,432,099 A | 7/1995 | Ekins | |
| 5,455,178 A | 10/1995 | Fattinger | |
| 5,523,089 A | 6/1996 | Bergstrom et al. | |
| 5,525,466 A | 6/1996 | Slovacek et al. | |
| 5,631,170 A | 5/1997 | Attridge | |
| 5,738,992 A | 4/1998 | Cook et al. | |
| 5,747,274 A | 5/1998 | Jackowski | |
| 5,807,755 A | 9/1998 | Ekins | |
| 5,814,565 A | 9/1998 | Reichert et al. | |
| 5,837,551 A | 11/1998 | Ekins | |
| 5,874,219 A | 2/1999 | Rava et al. | |
| 5,961,923 A | 10/1999 | Nova et al. | |
| 6,485,690 B1 | 11/2002 | Pfost et al. | |
| 6,653,151 B2 | 11/2003 | Anderson et al. | |

FOREIGN PATENT DOCUMENTS

| | | |
|---|---|---|
| EP | 0 093 613 | 11/1983 |
| WO | 84/01031 | 3/1984 |
| WO | 95/33197 | 12/1995 |
| WO | 95/33198 | 12/1995 |
| WO | 96/35940 | 11/1996 |
| WO | 97/35181 | 9/1997 |
| WO | 98/22799 | 5/1998 |
| WO | 98/29736 | 7/1998 |

OTHER PUBLICATIONS

International Search Report issued Jul. 29, 2002 in the International (PCT) Application No. PCT/EP 01/05995.
T.E. Plowman et al.: "Multiple-analyte Fluoroimmunoassay Using an Integrated Optical Waveguide Sensor"; Analytical Chemistry, American Chemical Society, Columbus, U.S., vol. 71, No. 19, Oct. 1, 1999, pp. 4344-4352,XP-000854131, ISSN: 0003-2700, whole document.
C. A. Rowe et al.: "Array Biosensor for Simultaneous Identification of Bacterial, Viral, and Protein Analytes", Analytical Chemistry, American Chemical Society, Columbus, U.S., vol. 71, 1999, pp. 3846-3854, XP-000996992, ISSN: 0003-2700, whole document.

L.G. Mendoza: "High-Throughput Microarray=Based Enzyme-Linked Immunosorbent Assay (ELISA)", Biotechniques, Eaton Publishing, Natick, U.S., vol. 27, No. 4, Oct. 1999, pp. 778-780, 782-786, 788, XP-000992893, ISSN: 0736-6205, whole document.

E. Schick et al.: "Ultrasensitive Multianalyte Immunoassays: The Synergy Between Planar Waveguide- and Microarray Technology", European Biophysics Journal, vol. 29, No. 4-5, Aug. 22, 2000, p. 379, XP-002205023, 3rd European Biophysics Congress; Munchen, Germany, Sep. 13, 2000, ISSN: 0175-7571, whole document.

* cited by examiner

*Primary Examiner*—Christopher L Chin
(74) *Attorney, Agent, or Firm*—Wenderoth, Lind & Ponack, L.L.P.

(57) ABSTRACT

The invention is related to different embodiments of a kit for the simultaneous qualitative and/or quantitative determination of a multitude of analytes comprising

- a sensor platform comprising an optical thin-film waveguide with a layer (a) transparent at least at an excitation wavelength on a layer (b) with lower refractive index than layer (a), also transparent at least at said excitation wavelength, and at least one grating structure (c) modulated in said layer (a), for the incoupling of said excitation light into layer (a),
- at least one array of biological or biochemical or synthetic recognition elements immobilized in discrete measurement areas (d) directly or by means of an adhesion-promoting layer on layer (a), for specific recognition and/or binding of said analytes and/or for specific interaction with said analytes,
- means for laterally resolved referencing of the excitation light intensity available in the measurement areas, and optionally
- means for the calibration of one or more luminescences generated in the near-field of layer (a) as a consequence of the binding of one or more analytes or of the specific interaction with one or more analytes, wherein a liquid sample to be analyzed for said analytes is brought into contact with said measurement areas on said sensor platform either directly or after mixture with further reagents. The invention is also related to analytical systems based on a kit according to the invention and to methods for the determination of one or more analytes, based on said kit, and to use thereof.

30 Claims, 4 Drawing Sheets

KIT AND METHOD FOR MULTI-ANALYTE DETERMINATION

This is a divisional of U.S. patent application Ser. No. 10/296,851, filed Nov. 27, 2002, now U.S. Pat. 7,396,675, which was the National Stage of International Application No. PCT/EP01/05995, filed May 25, 2001.

The invention is related to different embodiments of a kit for the simultaneous qualitative and/or quantitative determination of a multitude of analytes. The invention is also related to analytical system based on a kit according to the invention and methods for the determination of one or more analytes performed therewith, as well as their use.

For the determination of a multitude of analytes, currently mainly such methods are used, wherein the determination of different analytes is performed in discrete sample compartments or "wells" of so-called microtiter plates. The most common are plates with a pitch (geometrical arrangements in rows and columns) of 8×12 wells on a footprint of typically about 8 cm×12 cm, wherein a volume of some hundred microliters is required for filling a single well. It would be desirable for many applications, however, to determine several analytes simultaneously in a single sample compartment, using a sample volume as small as possible.

In U.S. Pat. No. 5,747,274, measurement arrangements and methods for the early recognition of cardiac infarctions, upon determination of several from at least three infarction markers, are described, wherein the determination of these markers can be performed in individual sample compartments or in a common sample compartment, a single (common) sample compartment being provided, according to the disclosure for the latter case, as a continuous flow channel, one demarcation of which being formed, for example, by a membrane, whereon antibodies for the three different markers are immobilized. However, there are no hints for an arrangement of several sample compartments or flow channels of this type on a common support. Additionally, there is no geometrical information concerning the size of the measurement areas.

In WO 84/01031, U.S. Pat. No. 5,807,755, U.S. Pat. No. 5,837,551, and in U.S. Pat. No. 5,432,099, immobilization of the specific recognition elements for an analyte in the geometry of small "spots", of partially significantly below 1 $mm^2$, on a solid support is proposed. The purpose of this immobilization geometry is to be able to determine the concentration of an analyte in a way, which is only dependent on the incubation time, but essentially independent from the absolute sample volume (in the absence of a continuous flow), upon binding only a small part of the analyte molecules that are present. The measurement arrangements disclosed in the related examples are based on determinations by fluorescence measurements in conventional microtiter plates. Thereby, also arrangements are described, wherein spots of up to three different, fluorescently labeled antibodies are measured in a common microtiter plate well. A minimization of the spot size would be desirable, following the theoretical argumentation in these patent specifications. The minimum signal height to be distinguished from the background signal, however, would set a lower limit for the spot size.

For achieving lower detection limits, in the last years numerous measurement arrangements have been developed, wherein the determination of an analyte is based on its interaction with the evanescent field, which is associated with light guiding in an optical waveguide, wherein biochemical or biological recognition elements for the specific recognition and binding of the analyte molecules are immobilized on the surface of the waveguide.

When a light wave is coupled into a planar thin-film waveguide surrounded by optically rarer media, i.e. media of lower refractive index, the light wave is guided by total reflection at the interfaces of the waveguiding layer. In that arrangement, a fraction of the electromagnetic energy penetrates the media of lower refractive index. This portion is termed the evanescent (=decaying) field. The strength of the evanescent field depends to a very great extent on the thickness of the waveguiding layer itself and on the ratio of the refractive indices of the waveguiding layer and of the media surrounding it. In the case of thin waveguides, i.e. layer thicknesses that are the same as or smaller than the wavelength of the light to be guided, discrete modes of the guided light can be distinguished. As an advantage of such methods, the interaction with the analyte is limited to the penetration depth of the evanescent field into the adjacent medium, being of the order of some hundred nanometers, and interfering signals from the depth of the (bulk) medium can be mainly avoided. The first proposed measurement arrangements of this type were based on highly multi-modal, self-supporting single-layer waveguides, such as fibers or plates of transparent plastics or glass, with thicknesses from some hundred micrometers up to several millimeters.

For an improvement of the sensitivity and simultaneously for an easier manufacturing in mass production, planar thin-film waveguides have been proposed. In the simplest case, a planar thin-film waveguide consists of a three-layer system: support material (substrate), waveguiding layer, superstrate (respectively the sample to be analyzed), wherein the waveguiding layer has the highest refractive index. Additional intermediate layers can further improve the action of the planar waveguide.

Several methods for the incoupling of excitation light into a planar waveguide are known. The methods used earliest were based on front face coupling or prism coupling, wherein generally a liquid is introduced between the prism and the waveguide, in order to reduce reflections due to air gaps. These two methods are mainly suited with respect to waveguides of relatively large layer thickness, i.e. especially self-supporting waveguides, and with respect to waveguides with a refractive index significantly below 2. For incoupling of excitation light into very thin waveguiding layers of high refractive index, however, the use of coupling gratings is significantly a more elegant method.

In this application, the term "luminescence" means the spontaneous emission of photons in the range from ultraviolet to infrared, after optical or other than optical excitation, such as electrical or chemical or biochemical or thermal excitation. For example, chemiluminescence, bioluminescence, electroluminescence, and especially fluorescence and phosphorescence are included commonly under the term "luminescence".

For achieving lower detection limits, luminescence-based methods appear as more adequate, because of higher selectivity of signal generation, than those methods which are based on a change of the effective refractive index/such as grating coupler sensors or methods based on surface plasmon resonance).

In this arrangement, luminescence excitation is limited to the penetration depth of the evanescent field into the medium of lower refractive index, i.e to immediate proximity of the waveguiding area, with a penetration depth of the order of some hundred nanometers into the medium. This principle is called evanescent luminescence excitation.

By means of highly refractive thin-film waveguides, based on an only some hundred nanometers thin waveguiding film on a transparent support material, the sensitivity could be increased considerably during the last years. In WO 95/33197, for example, a method is described, wherein the excitation light is coupled into the waveguiding film by a relief grating as a diffractive optical element. The surface of the sensor platform is contacted with a sample containing the analyte, and the isotropically emitted luminescence from substances capable of luminescence, that are located within the penetration depth of the evanescent field, is measured by adequate measurement arrangements, such as photodiodes, photomultipliers or CCD cameras. The portion of evanescently excited radiation, that has back-coupled into the waveguide, can also be out-coupled by a diffractive optical element, like a grating, and be measured. This method is described, for example, in WO 95/33198.

A disadvantage of all methods for the detection of evanescently excited luminescence describes as state of the art, especially in the specifications WO 95/33197 and WO 95/33198, is that always only one sample at a time can be analyzed on the waveguiding layer of the sensor platform, which layer is formed as a homogeneous film. In order to perform further measurements on the same sensor platform, tedious washing or cleaning steps are continuously required. This holds especially, if an analyte different from the one in the first measurement has to be determined. In case of an immunoassay this means in general, that the whole immobilized layer on the sensor platform has to be exchanged, or that even a whole new sensor platform has to be used. Thus, especially simultaneous determinations of multiple analytes cannot be performed.

For example in the specification WO 96/35940, arrangements (arrays) have been proposed, wherein at least two discrete waveguiding areas, to which excitation light is launched separately, are provided on one sensor platform, in order to perform exclusively luminescence-based, multiple measurements with essentially mono-modal, planar inorganic waveguides simultaneously or sequentially. A drawback resulting from the partitioning of the sensor platform into discrete waveguiding areas, however, is the relatively large need of space for discrete measurement areas in discrete waveguiding regions on the common sensor platform, because of which again only a relatively low density of different measurement areas (or so-called "features") can be achieved.

The use of the wording "locally (or laterally or spatially) separated measurement areas" or of "discrete measurement areas", according to the spirit of the present invention, will be defined more precisely in a later part of the invention.

Besides numerous other arrangements for the design of sample compartments for measurement arrangements for the determination of luminescence excited in the evanescent field of a planar waveguide, in WO 98/22799 also arrangements with the shape of known microtiter plates are proposed. The determination of multiple analytes upon their binding to different recognition elements immobilized within a single sample compartment, however, is also in this disclosure not been taken care of.

In U.S. Pat. Nos. 5,525,466 and 5,738,992, an optical sensor based on fluorescence excitation in the evanescent field of a self-supporting multi-mode waveguide, preferably of a fiber-optic type waveguide, is described. In-coupling of excitation light and out-coupling of fluorescence light back-coupled into the multi-mode waveguide are performed upon distal end in-coupling and out-coupling. Due to the operational principle of such multimode-waveguides, the fluorescence signal for analyte determination detected therewith is obtained as a single, integral value for the whole surface interacting with the sample. Mainly for the purpose of signal normalization, for example for taking into account surface defects with effects on the signals, fluorescent reference compounds are co-immobilized on the sensor surface, besides the biochemical or biological or synthetic recognition elements for the specific recognition and binding of an analyte to be determined. Due to the basic sensor principle, however, not a locally resolved, but only a normalization effecting a single, integral measurement value is possible. As a consequence, a determination of different analytes can only be performed upon using labels with different excitation wavelengths or by sequential measurements, after removing analytes bound before. Because of the above reasons, those arrangements, together with the described referencing method, do only hardly or even not appear as suited for the simultaneous determination of a multitude of analytes.

In U.S. Pat. No. 5,631,170 and European patent application No. 093,613 different methods of referencing, especially for sensors based on fluorescence excitation in the evanescent field of optical waveguides, are discussed. In European patent application No. 093,613 a method for referencing in a region adjacent to the "measurement area" is described. Especially, it is emphasized in that disclosure the necessity of using reference and (analyte) measurement signals from the same regions on a sensor platform. As a possible realization, kinetic (time-resolved) measurements are mentioned, because the kinetics of analyte binding is not dependent on the physical waveguide parameters and possible defects effecting the signals locally. As a disadvantage of the kinetic method, however, its dependence on external parameters, such as temperature and viscosity of the individual sample, is described. In U.S. Pat. No. 5,631,170 referencing by means of co-immobilized fluorophores is described, which generate a reference signal independent from the analyte concentration. It is preferred that the specific recognition elements for analyte binding and co-immobilized fluorophores for the purpose of referencing are provided in a statistical mixture on the sensor platform. Additionally, a method for simultaneous calibration is presented in the example of a "capillary fill device" (CFD) as an application, wherein (for example in a competitive immunoassay), in addition to the sample, known amounts of the analyte are applied in local regions of the CFD, for example upon dissolving these added known amounts of analyte from reagent compartments (for example located opposite to the sensor surface) dedicated for this purpose upon application of the sample.

In the international patent application WO 97/35181, methods for the simultaneous determination of one or more analytes are described, wherein, in a "well" formed in a waveguide (i.e. in the surface of said waveguide) patches with different recognition elements are deposited, which are brought into contact with a sample solution containing one or more analytes. For purposes of calibration, in parallel solutions with defined analyte concentrations are applied to further wells with similar patches. As an example, always 3 wells (for measurement of calibration solutions with high and low analyte concentrations and of the sample solution) with discrete patches and recognition elements different for different wells, for the parallel determination of multiple analytes, are presented. There are no hints towards locally resolved referencing.

In *Analytical Chemistry* Vol. 71 (1999) 4344-4352, a multi-analyte immunoassay on a silicon nitride waveguide is presented. Simultaneous determination of up to three analytes on three channel-like recognition regions (measurement areas) with different biological recognition elements is described. The analytes and tracer antibodies, in a mixture, are added to a sample cell covering the three measurement areas. The background is always determined in advance with a dedicated solution without analyte. Based on the disclosure, it is not clear if the background determination is performed locally resolved or integrally for the different measurement areas. For generation of a calibration curve a multitude of individual measurements on always new sensor platforms has to be performed, as the sensor platform is not regenerated. Facing the only small number of measurement areas on a sensor platform and the process resulting from the assay design, this has to be regarded as a disadvantage, as the precision of the method is reduced when using different sensor platforms and the duration of the method is considerably increased.

In *Analytical Chemistry* Vol. 71 (1999) 3846-3852, it is also presented a multi-analyte immunoassay for the simultaneous determination of three different analytes. *Bacillus globigii*, MS2 bacterio phages and staphylococcal enterotoxin B are used as examples of analytes of the groups bacteria, viruses, and proteins, wherein antibodies against these analytes have been immobilized always in two parallel rows (channels) on a glass plate acting as a (self-supporting multimode) waveguide. In the course of the multi-analyte assay described in the following of that disclosure, a flow cell with flow channels perpendicular to the rows of immobilized recognition elements is placed on the glass plate. The sandwich immunoassays are performed by sequential addition of washing solution (buffer), of the sample containing one or more analytes, of washing solution (buffer), of tracer antibodies (individually or as a cocktail mixture), and of washing solution (buffer). The measured local fluorescence intensities are corrected by subtraction of the background signals measured adjacent to the measurement areas. Also in this paper, there are no hints towards taking into account local variations of the excitation light intensity. Also that arrangement does not allow for performing a whole series of measurements for a simultaneous determination of multiple analytes, together with the necessary calibrations, but requires for such a purpose either the use of several different sensor platforms or repetitive, sequential measurements with intermediate regeneration on a platform, which is possible to only a limited extent especially in case of immunoassays.

In *Biotechniques* 27 (1999) 778-788, an arrangement with 96 wells, each with 4 arrays of 36 spots (i.e. 144 spots per well in total), on the footprint of a standard microtiter plate (about 8 cm×12 cm), for the development of ELISAs (enzyme-linked immunosorbent assays) based on micro-arrays, is presented. Out of the 6×6 measurement areas, always one row and one column is dedicated for "biotinylated BSA markers" for purposes of positioning and for the control of the efficacy of the reagents applied for the enzymatic detection step of the assay by addition of fluorescent "alkaline phosphatase substrate" (ELF®). —This arrangement indicates a possibility for a significant increase of the through-put of classical assays (ELISAs); the demonstrated sensitivity (13.4 ng/ml rabbit IgG), however, does not appear to be satisfactory.

In summary, it has to be noted that a common solution for the following tasks for a fast, simultaneous, highly sensitive determination of a multitude (i.e. three or more) analytes has so far not been provided:

Simultaneous determination of multiple analytes on one sensor platform with detection limits in the pico-molar range An assay protocol as simple as possible in order to minimize the requirements on the fluidics (e.g. by application of a mixture of a sample containing multiple analytes to be determined with several tracer molecules)

Locally resolved referencing for taking into account local variations of the excitation light intensity Optionally conducting of simultaneous calibration measurements on the same sensor platform.

Subject of the invention is a kit for the simultaneous qualitative and/or quantitative determination of a multitude of analytes comprising a sensor platform comprising an optical thin-film waveguide with a layer (a) transparent at least at an excitation wavelength on a layer (b) with lower refractive index than layer (a), also transparent at least at said excitation wavelength, and at least one grating structure (c) modulated in said layer (a), for the incoupling of said excitation light into layer (a), at least one array of biological or biochemical or synthetic recognition elements immobilized in discrete measurement areas (d) directly or by means of an adhesion-promoting layer on layer (a), for specific recognition and/or binding of said analytes and/or for specific interaction with said analytes, means for laterally resolved referencing of the excitation light intensity available in the measurement areas, and optionally means for the calibration of one or more luminescences generated in the near-field of layer (a) as a consequence of the binding of one or more analytes or of the specific interaction with one or more analytes, wherein a liquid sample to be analyzed for said analytes is brought into contact with said measurement areas on said sensor platform either directly or after mixture with further reagents.

The described tasks can be solved by the kit according to the invention. Especially it was found surprisingly, that a similar high sensitivity and reproducibility of the simultaneous determination of a multitude of analytes in a sample can be achieved in multi-analyte assays, upon using a kit according to the invention, as so far in a corresponding number of individual assays for the determination of the individual analytes.

In the spirit of this invention, spatially separated measurement areas (d) shall be defined by the area that is occupied by biological or biochemical or synthetic recognition elements immobilized thereon, for recognition of one or multiple analytes in a liquid sample. These areas can have any geometry, for example the form of dots, circles, rectangles, triangles, ellipses or lines.

It shall be understood under the attribute "optical transparency", that the material characterized by this attribute is essentially transparent and thus free of absorption at least at one or several excitation wavelengths used for the excitation of one or more luminescences.

For a given thickness of the optically transparent layer (a) the sensitivity of an arrangement according to the invention is the better, the higher the difference between the refractive indices of the layer (a) and the adjacent media is, i.e. the higher the refractive index of layer (a) is. It is preferred that the refractive index of the first optically transparent layer (a) is higher than 1.8.

A further important requirement on the properties of the layer (a) is, that the propagation losses of the light guided in said layer are as low as possible. It is preferred that the first optically transparent layer (a) comprises a material of the group of $TiO_2$, $ZnO$, $Nb_2O_5$, $Ta_2O_5$, $HfO_2$, or $ZrO_2$, especially preferred of $TiO_2$ or $Nb_2O_5$ or $Ta_2O_5$. Combinations of several such materials can also be used.

For a given material of the layer (a) and a given refractive index the sensitivity is the better, the smaller the layer thickness is, as long as the layer thickness is larger than a lower limiting value. The lower limiting value is determined by the cease of light-guiding upon decrease of the layer thickness below a value that is dependent on the wavelength of the light to be guided and by an increase of the propagation losses with decreasing layer thickness in case of very thin layers. It is of advantage, if the product of the thickness of layer (a) and its refractive index is one tenth up to a whole, preferably one third to two thirds of the excitation wavelength of an excitation light to be coupled into layer (a).

The optically transparent layer (b) should be characterized by low absorption and low fluorescence, in the ideal case free from absorption and fluorescence. Additionally, the surface roughness should be low, as the surface roughness of layer (b) does effect, dependent on the deposition process to a more or less pronounced extent, the surface roughness of a layer (a) intended as the waveguiding layer after its deposition. An increased surface roughness at the interfaces of layer (a) leads to increased scattering losses of the guided light, which, however, is undesired. These requirements are satisfied by a multitude of materials. It is preferred that the material of the second optically transparent layer (b) comprises silicates, e.g. glass or quartz, or a transparent thermoplastic or moldable plastics, e.g. of the group formed by polycarbonate, polyimide, acrylate, especially poly methylmethacrylate, or poly styrol. It is preferred that grating structures (c) modulated in layer (a) have a period of 200 nm-1000 nm and a modulation depth of 3 nm-100 nm, preferably of 10 nm-50 nm. Thereby, it is preferred that the ratio of the modulation depth and the thickness of the first optically transparent layer (a) is equal or smaller than 0.4.

The grating structure can be provided in different geometric forms. It is preferred that the grating structure (c) is a relief grating with any profile, for example with a rectangular, triangular or semi-circular profile, or a phase or volume grating with a periodic modulation of the refractive index in the essentially planar optically transparent layer (a).

For one embodiment of the arrangement it is preferred that the grating structure (c) is a diffractive grating with a uniform period.

For certain applications, for example for in-coupling excitation light of different wavelengths simultaneously, however, it can be of advantage, if the grating structure (c) is a multi-diffractive grating.

For certain embodiments it is preferred that the grating structure (c) has a periodicity that is laterally varying perpendicular or in parallel to the direction of propagation of the excitation light in-coupled into the optically transparent layer (a).

For many embodiments it is preferred that the sensor platform comprises even, non-modulated regions of the layer (a), which are preferably arranged in the direction of propagation of an excitation light in-coupled into the layer (a) by a grating structure (c) and guided in layer (a).

In general, grating structures (c) can be used for the in-coupling of excitation light towards the measurement areas (d) and/or for the out-coupling of luminescence light back-coupled into the layer (a).

As a general embodiment, the sensor platform therefore comprises a multitude of grating structures (c) of similar or different periods, optionally with adjacent even, non-modulated regions of the layer (a) on a common, continuous substrate.

For the assay applications using a kit according to the invention, it is generally advantageous to in-couple a suitable excitation light by means of a grating structure (c), to which is adjacent, in the direction of propagation of the in-coupled light guided in layer (a), an unmodulated region of the layer (a) with a multitude of measurement areas in an array located thereon. It is advantageous if another grating structure with an adjacent further array of measurement areas is provided adjacent to that first grating structure and that first array of measurement areas, in the direction of propagation of the guided light, etc. After passing a non-modulated region, the light guided in layer (a) will always be out-coupled again. In the direction perpendicular to the direction of propagation of the guided light (i.e., in parallel to the grating lines) will be provided further arrays of measurement areas. Therefore, it is preferred that a dedicated grating structure (c) for out-coupling of the guided excitation light is provided following, in direction of propagation of the in-coupled excitation light, each array of measurement areas, wherein, perpendicular to the direction of propagation of the in-coupled excitation light, individual grating structures for different arrays can be provided, or these grating structures can also extend in this direction (perpendicular to the direction of propagation of the in-coupled excitation light) over the whole sensor platform. This means, that the in-coupling grating for an array following in direction of propagation of the excitation light guided in layer (a) of a sensor platform is used as an out-coupling grating for the excitation light that has been in-coupled at the in-coupling grating of the array preceding in said direction of propagation.

For certain applications, for example when using two or more luminescence labels with different excitation wavelengths, it is advantageous if the grating structure is a superposition of two or more grating structures of different periodicities for the in-coupling of excitation light of different wavelengths, the grating lines being orientated parallel or not parallel, preferably not parallel, to each other, wherein in case of two superimposed grating structures their grating lines are preferably perpendicular to each other.

The partitioning of the sensor platform into sections with grating structures modulated therein and adjacent non-modulated sections means for the practice, that the area requirements for a single array of measurement areas between two consecutive grating structures (including at least one grating structure dedicated for said array) cannot be reduced below a certain minimum, which is of the order of 0.1 mm$^2$ to 1 mm$^2$, facing the current technical capabilities for the manufacture of the grating structures and for the in-coupling of a suited excitation light bundle. Therefore it is advantageous especially for arrangements, where a multitude of small-area arrays is desired, if a grating structure (c) or a superposition of several grating structures in the layer (a) is modulated essentially across the whole area of the sensor platform.

For a special embodiment of the invention it is preferred, that optically or mechanically recognizable marks for simplifying adjustments in an optical system and/or for the connection to sample compartments as part of an analytical system are provided on the sensor platform.

If an autofluorescence of layer (b) cannot be excluded, especially if it comprises a plastic such as polycarbonate, or for reducing the effect of the surface roughness of layer (b) on the light guiding in layer (a), it can be advantageous, if an intermediate layer is deposited between layers (a) and (b). Therefore, it is characteristic for another embodiment of the arrangement according to the invention, that an additional optically transparent layer (b') with lower refractive index than layer (a) and in contact with layer (a), and with a thickness of 5 nm-10 000 nm, preferably of 10 nm -1000 nm, is located between the optically transparent layers (a) and (b).

The simplest method of immobilization of the biological or biochemical or synthetic recognition elements consists in physical adsorption, for example due to hydrophobic interaction between the recognition elements and the base plate. However, the extent of these interactions can be effected strongly by the composition of the medium and its physical-chemical properties, such as polarity and ionic strength. Especially in case of sequential addition of different reagents in a multi-step assay, the adhesion of the recognition elements on the surface, after only adsorptive immobilization, is often insufficient. In a preferred embodiment of the kit according to the invention, the adhesion is improved by deposition of an adhesion-promoting layer (f) on the base plate for the immobilization of the biological or biochemical or synthetic recognition elements. Especially in case of biological or biochemical recognition elements to be immobilized, the adhesion-promoting layer can also contribute to improve the "biocompatibility", i.e. to preserve the binding capability of the recognition elements, in comparison with the binding capability of these recognition elements in their natural biological or biochemical environment, and to avoid a denaturation. It is preferred, that the adhesion-promoting layer (f) has a thickness of less than 200 nm, preferably of less than 20 nm. For the generation of the adhesion-promoting layer, many materials can be used. Without any restriction, it is preferred, that the adhesion-promoting layer (f) comprises one or more chemical compounds from the groups comprising silanes, epoxides, functionalised, charged or polar polymers, and "self-organized passive or functionalized mono- or double-layers".

An important aspect of the kit according to the invention is, that the biological or biochemical or synthetic recognition elements are immobilized in discrete (laterally separated) measurement areas (d). These discrete measurement areas can be formed by spatially selective deposition of the biological or biochemical or synthetic recognition elements on the sensor platform. Numerous methods can be used for the deposition. It is preferred without any restriction of generality, that the biological or biochemical or synthetic recognition elements are deposited on the sensor platform by one or more methods from the group of methods comprising "ink jet spotting, mechanical spotting by means of pin, pen or capillary, "micro contact printing", fluidically contacting the measurement areas with the biological or biochemical or synthetic recognition elements upon their supply in parallel or crossed micro channels, upon exposure to pressure differences or to electric or electromagnetic potentials, and photochemical or photolithographic immobilization methods.

As said biological or biochemical or synthetic recognition elements, components from the group comprising nucleic acids (e.g. DNA, RNA, oligonucleotides) and nucleic acid analogues (e.g. PNA), mono- or polyclonal antibodies, peptides, enzymes, aptamers, synthetic peptide structures, soluble membrane-bound proteins and proteins isolated from a membrane, such as receptors, their ligands, antigens for antibodies, "histidin-tag components" and their complex forming partners, cavities generated by chemical synthesis, for hosting molecular imprints. etc., are deposited. It is also intended that whole cells, cell components, cell membranes or their fragments are deposited as biological or biochemical or synthetic recognition elements.

A further special embodiment of the kit according to the invention is characterized, in that the density of the recognition elements immobilized in discrete measurement areas for the detection of different analytes on different measurement areas is selected in such a way, that, upon determination of different analytes in a common array, the luminescence signals are of similar order of magnitude, i.e., that the related calibration curves for the analyte determinations to be performed simultaneously can be recorded without a change of the opto-electronic system adjustments.

For several applications it is preferred that wherein arrays of measurement areas are arranged in segments of one or more measurement areas for analyte determination and of measurement areas for referencing, i.e. for the determination of physical parameters and/or of chemical differences between different applied samples. Thereby, one or more arrays can comprise segments of two or more measurement areas with biological or biochemical or synthetic recognition elements for analyte determination or for referencing, that are similar within said segment. However, a segment can also comprise several discrete measurement areas with recognition elements that are different from each other.

It is characteristic for one possible embodiment of a kit according to the invention, that one or more segments of an array or one or more arrays are provided for the determination of analytes of a common group, such as using immobilized anti-cytokine antibodies for the determination of different cytokines. In a similar way, one or more segments of an array or one or more arrays can be used for the simultaneous determination of a whole set of so-called "marker proteins". This can be, for example, occurring intra-cellular or extra-cellular in a body, which are, for example, apparent at an elevated concentration, caused by and indicative for certain diseases, such as degenerative diseases, certain cancer types or autoimmune diseases.

A recognition element for the determination of an analyte and to be immobilized is typically in such a way, that it shows a specificity and binding affinity for said analyte as high as possible and has a cross-reactivity to other analytes that might be (bio)chemically similar to said analyte as low as possible. For certain application, for example the determination of low-molecular compounds in immuno analytics or the detection of single-point mutations in nucleic acid analytics, a cross-reactivity with the (bio)chemically most similar compounds can hardly be avoided. For such applications, an embodiment of the kit according to the invention can be advantageous, wherein one or more measurement areas of a segment or of an array are provided for the same analyte, and wherein the related immobilized biological or biochemical recognition elements have different affinities for said analyte. Thereby it is convenient, if the recognition elements are selected in such a way that their affinities to different, but (bio)chemically rather similar analytes, change from recognition element to recognition element in a different, characteristic manner. Then the identity of the analyte can be determined from the totality of the signals from different measurement areas with different recognition elements for a single analyte, in a similar way like a finger print.

Another embodiment is characterized in that one or more segments of an array or that one or more arrays are provided for the determination of different groups of analytes, such as the determination of pharmaceutical drugs for the treatment of a disease and/or of their metabolites and/or of the indicator compounds for said disease like so-called "marker proteins".

This enables to determine the concentrations of a whole set of "marker proteins", as described above, as well as the concentrations of drugs administered for disease treatment and of their metabolic products in a single measurement. Due to the variety of possible combinations, there is a large potential, for example for an acceleration of pharmaceutical product development or of patient stratification for the determination of an optimum drug treatment.

For certain applications, where, for example, aspects of the reproducibility of the results from a multitude of arrays on a common sensor platform are of high priority, it is advantageous, if two or more arrays have a similar geometrical arrangement of measurement areas and/or of segments of measurement areas for the determination of similar analytes on said arrays.

For other applications it is important to minimize effects of systematic errors on the results, as they can occur, for example, upon replication of similar structures on a common sensor platform. For example for such an application it can be advantageous, if two or more arrays have a different geometrical arrangement of measurement areas and/or of segments of measurement areas for the determination of similar analytes on said arrays.

The kit according to the invention, with a multitude of measurement areas in discrete arrays, of which again a multitude can be provided on a common sensor platform, opens up the possibility to perform also many types of duplications or multiple replications of similar measurements under essentially identical conditions, upon using relatively small amounts of sample solutions, reagents and optionally calibration solutions on one and the same platform. Thus, for example, statistical data can be generated in a single measurement, which would require traditionally a multitude of individual measurements, with a correspondingly longer total measurement time and larger consumption of sample and reagent amounts. It is preferred, that two or more identical measurement areas are provided for the determination of each analyte or for physical or chemical referencing within a segment or an array. Thereby, said identical measurement areas can, for example, be arranged in a continuous row or column or diagonal of an array or a segment of measurement areas. The aspects of referencing can be related to physical or chemical parameters of the sensor platform, such as local variations of the excitation light intensity (see also below), as well as effects induced by the sample, like its pH, ionic strength, refractive index, temperature, etc.

On the other hand, for other applications it can also be advantageous, if said identical measurement areas are distributed statistically within an array or a segment of measurement areas.

In general, the immobilized recognition elements are selected in such a way, that they recognize and bind the analyte to be determined with a specificity as high as possible. Typically however, it must be expected that also a nonspecific adsorption of analyte molecules on the surface of the base plate does occur, especially if there are still empty sites between the recognition elements immobilized in the measurement areas. Therefore it is preferred, that regions between the laterally separated measurement areas are "passivated" for minimization of non-specific binding of analytes or their tracer compounds, i.e., that compounds, that are "chemically neutral" towards the analyte, are deposited between the laterally separated measurement areas (d), preferably for example out of the groups formed by albumins, especially bovine serum albumin or human serum albumin, casein, unspecific polyclonal or monoclonal, alien or empirically unspecific antibodies for the one or the multiple analytes to be determined (especially for immuno assays), detergents—such as Tween 20®—fragmented natural or synthetic DNA not hybridizing with polynucleotides to be analyzed, such as extract from herring or salmon sperm (especially for polynucleotide hybridization assays), or also uncharged but hydrophilic polymers, such as poly ethyleneglycols or dextranes.

As described above, such an embodiment of the kit according to the invention, wherein an adhesion-promoting layer is deposited on the sensor platform before immobilization of the biological or biochemical or synthetic recognition elements, is advantageous for many, if not the majority of applications. Thereby such embodiments are preferred, wherein the function of passivation of regions between the laterally separated measurement areas for minimization of analytes or of their tracer compounds is fulfilled by the deposition of said adhesion-promoting layer on the sensor platform, without deposition of additional compounds.

The kit according to the invention can comprise a very large number of individual measurement areas. It is preferred that up to 100,000 measurement areas are provided in a 2-dimensional arrangement, and that a single measurement area has an area of 0.001 mm$^2$-6 mm$^2$.

A further subject of the invention is an embodiment of the kit according to the invention, wherein the upper surface of the sensor platform, with the measurement areas generated thereon, on the optically transparent layer (a), is combined with a further body in such a way, that one or more spatial recesses (cavities) for the generation of one or more sample compartments fluidically sealed against one another are formed between the sensor platform as the baseplate and said body, said sample compartments comprising each one or more measurement areas or segments or arrays of measurement areas. Thereby, as said body to be combined with the sensor platform, are understood according to the invention not only self-supporting structures, but also, for example, deposited structured coatings, optionally as thin as micrometers, which prevent a migration of liquid from a (in this case typically open) sample compartment thus provided to an adjacent sample compartment, at the conditions of use of the kit.

Characteristic for another embodiment is, that the sample compartments are provided as flow cells fluidically sealed against each other, each provided with at least one inlet and at least one outlet, and wherein optionally additionally at least one outlet of each flow cell leads to a fluidically connected reservoir operable to receive liquid exiting the flow cell.

Thereby it is advantageous, if the optional additional reservoir for receiving liquid exiting the flow cell is provided as a recess in the outer wall of the body combined with the sensor platform as the base plate.

There are several technical solutions for the generation of the cavities between the sensor platform as the base plate and the body combined therewith. In one possible arrangement, three-dimensional structures, with the pitch (geometrical arrangement in rows and/or columns) of the arrays of flow cells to be generated, are formed on the sensor platform as the base plate. These structures on the base plate can, for example, form the walls or parts of the walls, such as sockets, between flow cells adjacent to each other, which flow cells are formed by combination of the base plate with an adequately formed body. For generation of the array of flow cells it is also possible, that, for generation of the cavities between the sensor platform as the base plate and the body combined therewith, recesses are provided in the sensor platform.

Characteristic for another embodiment is, that, for generation of the cavities between the base plate and the body combined therewith, recesses are provided in said body.

The body to be combined with the base plate for the generation of the array of flow cells can consist of a single workpiece. In another embodiment, the body combined with the base plate is formed from several parts, wherein the combined parts of said body preferably form an irreversibly combined unit.

It is preferred, that the body combined with the base plate comprises auxiliary means facilitating the combination of said body and the base plate.

It is further preferred that the arrangement comprises a multitude, i.e., 2-2000, preferably 2-400, most preferably 2-100 sample compartments.

For example for applications, where the applications of the samples and/or of the reagents shall be performed directly by means of a dispenser, it is preferred that the sample compartments are open at the opposite side, with respect to the measurement areas, of the body combined with the sensor platform as the base plate.

It is preferred that the pitch (geometrical arrangement in rows and/or columns) of the sample compartments does correspond to the pitch (geometrical arrangement) of the wells of a standard microtiter plate.

Characteristic for another embodiment of arrangement of sample compartments as a part of the kit according to the invention is, that it is closed with an additional covering top, for example a film, a membrane or a cover plate.

The capacity of the flow cells can be varied within a large range upon variation of the size of the base areas and of the depth of the recesses, so that the inner volume of each sample compartment is typically 0.1 µl-1000 µl, preferably 1 µl-20 µl. Thereby, the inner volumes of different flow cells can be similar or different.

It is preferred, that the depth of the cavities between the sensor platform as the base plate and the body combined with said base plate is 1-1000 µm, preferably 20-200 µm. The size of the cavities of an array can be uniform or diverse and the base areas can have any geometry, preferably rectangular or polygonal or also other geometry. The lateral dimensions of the base areas can be varied within a large range as well, wherein typically the base areas of the cavities between the base plate and the body combined with said base plate are 0.1 mm$^2$-200 mm$^2$, preferably 1 mm$^2$-100 mm$^2$. It is preferred, that the corners of the base areas are rounded. Rounded corners effect the flow profile in a favorable way and facilitate the removal of gas bubbles that might be formed, respectively prevent their formation.

For the simultaneous supply of samples or reagents to a multitude of sample compartments, multi-channel pipettors for manual or automated reagent administration can be used, wherein the individual pipettes are arranged in one- or two-dimensional arrays, provided that the inlets of the arrangement of sample compartments according to the invention are arranged in the same pitch (geometrical arrangement in rows and/or columns). Preferably, therefore, the pitch of the arrangement does correspond to the pitch of the wells of a standard microtiter plate. Thereby, an arrangement of 8×12 wells at a (center-to-center) distance of about 9 mm is established as the industrial standard. Smaller arrays with, for example, 3, 6, 12, 24 and 48 wells, arranged at the same distance, are compatible with this standard. Several arrangements of sample compartments, according to the invention, provided as smaller arrays of flow cells, can also be combined in such a way, that the individual inlets of said flow cells are located at a whole-numbered multiple of the distance of about 9 mm.

Recently, also plates with 384 and 1536 wells, as a whole-numbered multiple of 96 wells on the same foot print at a correspondingly reduced well-to-well distance, are used, which shall also be called standard microtiter plates. By adaptation of the pitch of the sample compartments in the arrangement according to the invention, including the in- and outlets of each flow cells, to these standards, numerous commercially established and available laboratory pipettors and robots can be used for sample supply.

It is preferred, that the exterior dimensions of the arrangement of sample compartments, as a part of the kit according to the invention, do correspond to the foot print of these standard microtiter plates.

A further special embodiment of the invention is an arrangement with, for example, 2 to 8 sample compartments, as part of a kit according to the invention, in a column, with the properties as described above, or, for example, 2 to 12 sample compartments in a row, which themselves are combined with a carrier ("meta-carrier") with the dimensions of standard microtiter plates in such a way, that the pitch (geometrical arrangement in rows and/or columns) of the inlets of the flow cells does correspond to the pitch (geometrical arrangement) of the wells of a standard microtiter plate.

The adjoining of the arrangement of sample compartments with the meta-carrier can, for example, be performed by glueing or by exact fitting without glueing, if it is intended for single-use, or, for example by latching or inserting, if it is intended for multiple use. The material of the meta-carrier can, for example, be selected from the group comprising formable, moldable or millable plastics, metals, silicates, such as glass, quartz or ceramics.

Several rows or columns of such sample compartments can also be combined with a single meta-carrier in such a way, that the pitch (geometrical arrangement in rows and/or columns) of the inlets of the flow cells does correspond to the pitch (geometrical arrangement) of the wells of a standard microtiter plate, i.e., to a whole-numbered multiple of 9 mm (corresponding to a 96-well plate) or of 4.5 mm (corresponding to a 384-well plate, see above) or of 2.25 mm (corresponding to a 1536-well plate, see above).

Of course, the arrangement of sample compartments according to the invention can also be arranged in another pitch (geometry).

The materials for the body combined with the sensor platform as the base plate and the optional additional covering top have to satisfy the requirements of the actually intended application. Dependent on the specific application, these requirements are related to chemical and physical stability, for example upon exposure to acidic or basic media, salts, alcohols or detergents as parts of aqueous solutions, or to formamide, to stability upon temperature variations (e.g. between −30° C. and 100° C.), to thermal expansion coefficients of the base plate and of the body combined therewith as similar as possible, to optical properties (such as non-fluorescence, reflectivity), to mechanical workability, etc. It is preferred, that the material of the body combined with the base plate, as well as of an optional additional covering top is selected from the same group as the material of the meta-carrier. Thereby, the aforementioned components (the body combined with the sensor platform as the base plate, covering top) can be composed of a uniform material or can comprise a mixture or a composition, adjoined in layers or laterally of different materials, wherein the materials can substitute each other.

A very important aspect of the current invention is related to the possibilities for the locally resolved referencing of the available excitation light intensity. In case of traditional arrangements, with irradiation of the excitation light in a configuration of epi-illumination or transmission illumination, the available excitation light intensities of an irradiated area are mainly determined by the excitation light density in the cross-section of the excitation light bundle. In this case, local variations of the properties of the illuminated surface (such as a glass plate) have only a second order effect. However, in case of the kit according to the invention, local variations of the physical parameters of the sensor platform, such as the in-coupling efficiency of the grating structure (c) for the in-coupling of the excitation light into the optically transparent layer (a), or local variations of the propagation losses of a mode guided in the optically transparent layer (a), are of main importance.

Therefore, a further important subject of the invention are such embodiments of a kit according to the invention, wherein the means for the laterally resolved referencing of the excitation light intensity available in the measurement areas comprise the simultaneous or sequential generation of an image of the light emanating from the sensor platform at the excitation wavelength. Thereby it is presumed that the propagation losses are essentially proportional to the locally guided light intensity. The propagation losses are mainly determined by the surface roughness and homogeneity of the optically transparent layer (a) and of the substrate located beneath (optically transparent layer (b)). Especially, this type of referencing allows to take into account a local decrease of the locally available excitation light intensity in the direction of its propagation, if this decrease, for example, occurs due to an absorption of excitation light caused by a high local concentration of molecules in the evanescent field of the layer (a), which are absorbent at the excitation wavelength.

However, the assumption of the proportionality of the emitted scattered light to the intensity of the guided light is not valid at those locations, where an emission (out-coupling occurs due to local macroscopic scattering centers in contact with the layer (a). At these locations, the emitted scattered light is significantly stronger than proportional in comparison to the guided light. Therefore, its is also advantageous, if the means for the laterally resolved referencing of the excitation light intensity available in the measurement areas comprise the simultaneous or sequential generation of an image of the light emanating from the sensor platform at the luminescence wavelength. Of course, both methods can also be combined. Upon generation of a reference image, different effects of the imaging optics on the collection of the measurement signals shall be excluded. Therefore it is preferred, that the generation of an image of the excitation light emanating from the sensor platform is performed using the same optical path as for the collection of the luminescences emanating from the measurement areas.

Characteristic for another embodiment is, that the means for the laterally resolved referencing of the excitation light intensity available in the measurement areas comprise the simultaneous or sequential generation of an image of the light emanating from the sensor platform at another excitation wavelength as used for excitation of a luminescence. Thereby, it is preferred, that such an excitation wavelength is selected, at which molecules capable of, which are applied in the course of the method for the determination of one or more analytes or for purposes of referencing or calibration, do not show absorption or an absorption as low as possible, in order to avoid or minimize effects of "photochemical bleaching".

Additionally, it is preferred that the local resolution of the image for referencing the excitation light emanating from the sensor platform is below 100 μm, preferably below 20 μm. It is also preferred, that the means for the laterally resolved referencing of the excitation light intensity available in the measurement areas comprise the determination of the background signal at the actual luminescence wavelength between or adjacent to the measurement areas.

A characteristic, preferred embodiment of the kit according to the invention is, that the laterally resolved referencing of the excitation light intensity available in the measurement areas is performed by means of "luminescence marker spots", i.e., of the luminescence intensity from measurement areas with pre-immobilized luminescently labeled molecules (i.e., which molecules have been deposited in these measurement areas already before supply of a sample). Thereby, it is preferred that the "luminescence marker spots" are provided as a screen spreading over the whole sensor platform.

As described further below in more detail, preferably locally resolving detectors, such as CCD cameras (CCD: charge-coupled device) are used for signal detection. It is characteristic for these detectors, that their photo-sensitive elements (pixels) deliver a certain (mainly temperature-dependent) background signal defining the lower threshold for the detection of a local light signal and have also a maximum capacity (saturation) for the detection of high light intensities. For a given exposure time, the dynamic range for signal detection is defined by the difference between these threshold values. Both the luminescence signals for analyte detection and the reference signals should be within this dynamic range. Thereby it is advantageous, if both signals are of a similar order of magnitude, i.e. for example, if they differ by not more than one or more decades. According to the invention, this can be achieved, for example, if the density of the luminescently labeled molecules within a "luminescence marker spot" is selected, upon mixing with similar, but non-labeled molecules for immobilization, in such a way that the luminescence intensity from the regions of the "luminescence marker spots" is of similar order of magnitude as the luminescence intensity from the measurement areas dedicated for an analyte determination.

Preferably, the density and the concentration of the luminescently labeled molecules within a "luminescence marker spot" shall be alike within an array, preferably uniform on the whole sensor platform.

In case of this type of referencing, the local resolution is mainly determined by the density of the "luminescence marker spots" within an array respectively on the whole sensor platform. Preferably, the distance between and/or the size of different "luminescence marker spots" are adapted to the desired local resolution of the determination of the luminescence intensities from the discrete measurement areas.

It is preferred, that each array on the sensor platform comprises at least one "luminescence marker spot". It is advantageous, if at least one "luminescence marker spot" is provided adjacent to each segment of measurement areas for analyte determination.

There is a variety of possibilities for the geometrical arrangement of the "luminescence marker spots" within an array respectively on the sensor platform. A possible arrangement is for example, that each array comprises a continuous row and/or column of "luminescence marker spots" in parallel and/or perpendicular to the direction of propagation of the in-coupled excitation light, for determination of the two-dimensional distribution of the in-coupled excitation light in the region of said array.

It is intended that the means for the laterally resolved referencing of the excitation light intensity available in the measurement areas comprise the determination of an average of multiple locally resolved reference signals.

A further characteristics of the kit according to the invention is related to means for calibrating luminescence signals measured in the presence of one or more luminescence signals. As a possible embodiment, said means for the calibration of one or more luminescences generated in the near-field of layer (a), as a consequence of the binding of one or more analytes or of the specific interaction with one or more analytes, comprise the application of calibration solutions with known concentrations of the analytes to be determined to a pre-determined number of arrays. For example, 8-12 arrays of a sensor platform can be dedicated for purposes of calibration.

The kit according to the invention enables another opportunity not described so far, based on the multitude of measurement areas on one sensor platform. As this opportunity, it is not necessary to apply a multitude of calibration solutions of different known concentrations on one or more arrays, but possible to immobilize the biological or biochemical or synthetic recognition elements applied for the analyte detection at known, but different local concentration in the measurement areas dedicated for calibration purposes. As well as it is possible to generate a calibration curve by application of different calibration solutions with different analyte concentrations on an array with recognition elements with a single, uniform immobilization density, it is in principal possible to generate such a standard curve representing the binding activity and the multitude of binding events between an analyte and its recognition elements by application of a single calibration solution on an array with recognition elements provided at a different immobilization density. It is important for this simplified type of calibration, that the binding behavior between an analyte and its recognition elements is well-known, and that the variation, i.e., the difference between the lowest and the highest immobilization density in the measurement areas dedicated for an analyte is large enough for the calibration, in order to cover the whole intended application range of an assay for the analyte detection.

Therefore a further subject of the invention is a kit, wherein in one or more arrays always several measurement areas with biological or biochemical or synthetic recognition elements immobilized therein at a different, controlled density are provided, for the determination of an analyte that is common for these measurement areas. Thereby, it is especially preferred, that a calibration curve for an analyte can already be established upon application of a single calibration solution to an array comprising biological or biochemical or synthetic recognition elements for said analyte, immobilized in different measurement areas of that array at a sufficiently large "variation" of different controlled density, the concentration dependence of the signals indicative for the binding between said analyte and said biological or biochemical or synthetic recognition elements being known.

In another embodiment of the kit according to the invention always several measurement areas of different size (diameter) are intended for the determination of one or more analytes. This embodiment allows for an increase of the dynamic range for the determination of said analytes, due to the known fact, that the signal intensity to be expected (signal height per area unit of the dedicated measurement area) increases with decreasing area of said measurement area.

According to the invention there is another embodiment, wherein one or more arrays comprise one or more measurement areas dedicated for the determination of an analyte added to the sample at a known concentration, for purposes of calibration. This embodiment is comparable with the addition of so-called standards in analytical separation methods. Also for this embodiment it is a prerequisite, that the binding behavior between the analyte, to be added to one or all samples, and the immobilized recognition elements is well-known. Then, for example, from differences of the binding signals for this known additional analyte (e.g. resulting from variations of the physical properties of the sample, such as viscosity etc.) it can be extrapolated to corresponding differences of the binding behavior of the analytes of unknown concentrations to be determined. This embodiment is especially suited for a combination described before.

A further subject of the invention is an analytical system with any given embodiment of a kit according to the invention, additionally comprising at least one detector for the determination of one or more luminescences emanating from the grating waveguide structure (sensor platform).

Especially subject of the invention is an analytical system for the determination of one or more luminescences comprising
  at least one excitation light source
  a kit according to the invention
  at least one detector for detection of the light emanating from one or more measurement areas (d) on the sensor platform.

Characteristic for one possible embodiment of the analytical system according to the invention is, that the excitation light is irradiated towards the measurement areas in an epi-illumination or trans-illumination configuration.

It is preferred that the detection of the luminescence light is performed in such a way, that luminescence light out-coupled by a grating structure (c) or (c') is collected by the detector as well.

Characteristic for a preferred embodiment of the analytical system according to the invention is, that wherein the excitation light emitted from the at least one light source is essentially parallel and is irradiated at the resonance angle for in-coupling into the optically transparent layer (a) onto a grating structure (c) modulated in the layer (a).

As one possibility, the excitation light from at least one light source is expanded to an essentially parallel ray bundle by an expansion optics and irradiated at the resonance angle for in-coupling into the optically transparent layer (a) onto a large-size grating structure (c) modulated in the layer (a).

Characteristic for another embodiment is, that the excitation light from at least one light source is divided, by means of one or, in case of several light sources, by means of multiple diffractive optical elements, preferably Dammann gratings, or refractive optical elements, preferably micro-lens arrays, into a multitude of individual beams, with as similar intensity as possible of the individual beams originating from a common light source, which individual beams are irradiated essentially in parallel to each other onto grating structures (c) at the resonance angle for in-coupling into the layer (a).

Characteristic for an improvement is, that two or more light sources with the same or different emission wavelength are used as excitation light sources.

It is preferred, that at least one locally resolving detector is used for detection, for example of the group formed by CCD cameras, CCD chips, photodiode arrays, Avalanche diode arrays, multi-channel plates, and multi-channel photomultipliers. The invention includes analytical systems, which are characterized in that optical components of the group comprising lenses or lens systems for the shaping of the transmitted light bundles, planar or curved mirrors for the deviation and optionally additional shaping of the light bundles, prisms for the deviation and optionally spectral separation of the light bundles, dichroic mirrors for the spectrally selective deviation of parts of the light bundles, neutral density filters for the regulation of the transmitted light intensity, optical filters or monochromators for the spectrally selective transmission of parts of the light bundles, or polarization selective elements for the selection of discrete polarization directions of the excitation or luminescence light are located between the one or more excitation light sources and the sensor platform and/or between said sensor platform and the one or more detectors.

Light excitation can be performed continuously. It is preferred, however, that the excitation light is launched in pulses with duration of 1 fsec to 10 min.

Characteristic of an advanced embodiment of the analytical system is, that the emission light from the measurement areas is measured time-resolved.

In one embodiment of the analytical system according to the invention, launching and detection of the emission light is performed simultaneously for all measurement areas. Characteristic of another embodiment is, that launching of the excitation light and detection of the emission light from the one or more measurement areas is performed sequentially for one or more sample compartments. It is also possible, that sequential launching of the excitation light and detection of the emission light from one or more measurement areas is performed several times within a single sample compartment.

Thereby it is preferred, that sequential excitation and detection is performed using movable optical components of the group comprising mirrors, deviating prisms, and dichroic mirrors. Sequential excitation and detection can also be performed using movable glass fibers (optical fibers) glass fiber bundles (optical fiber bundles) for guiding the excitation light respectively luminescence light sequentially towards the one or more measurement areas respectively away from them.

In case of sequential detection of luminescence from different measurement areas a locally resolving detector is not mandatory, but, in such a case, a simple (locally not resolving) detector, such as a conventional photomultiplier or a photodiode or an avalanche photodiode can be used.

It is preferred in especial, that sequential excitation and detection is performed using an essentially focus and angle preserving scanner.

Characteristic of another embodiment of an analytical system with sequential excitation and detection is, that the arrangement, according to any of the aforementioned embodiments, is moved between steps of sequential excitation and detection.

It is also preferred that the analytical system according to the invention additionally comprises supply means for bringing the one or more samples into contact with the measurement areas on the sensor platform.

As one possible embodiment, the sample compartments have openings for locally addressed supply or removal of the samples or of the reagents at the side facing away from the optically transparent layer (a).

Characteristic for an improvement of the analytical system is, that compartments for reagents are provided, which reagents are wetted and brought into contact with the measurement areas during the course of the method for the determination of the one or more analytes. Characteristic for a special embodiment is, that these additional compartments for said reagents are provided in the body to be combined with the sensor platform as the base plate.

A further subject of the invention is a method for the simultaneous qualitative and/or quantitative determination of a multitude of analytes using a kit according any of the embodiments described above and/or using an analytical system according to the invention, wherein one or more liquid samples to be analyzed for said analytes are brought into contact with the measurement areas of a sensor platform, as a part of said kit, the excitation light intensity available in said measurement areas is referenced in a locally resolved way, and wherein optionally one or more luminescences generated in the near-field of the layer (a), from the measurement areas brought into contact with said sample or with said samples and resulting from the binding of one or more analytes to the biological or biochemical or synthetic recognition elements immobilized in said measurement areas or from the interaction between said analytes and said immobilized recognition elements, are calibrated.

It is preferred that the excitation light is in-coupled into the optically transparent layer (a) towards the measurement areas by the grating structure (c).

Characteristic for one possible embodiment of the method according to the invention is, that the sensor platform comprises even, non-modulated regions of the layer (a), which are preferably arranged in the direction of propagation of an excitation light in-coupled into the layer (a) by a grating structure (c) and guided in layer (a).

It is preferred, that (firstly) the isotropically emitted luminescence or (secondly) luminescence that is in-coupled into the optically transparent layer (a) and out-coupled by a grating structure (c) or luminescence comprising both parts (firstly and secondly) is measured simultaneously.

It is also part of the invention, that for the generation of said luminescence, a luminescent dye or a luminescent nano-particle is used as a luminescence label, which can be excited and emits at a wavelength between 300 nm and 1100 nm.

It is preferred, that the luminescence label is bound to the analyte or, in a competitive assay, to an analyte analogue or, in a multi-step assay, to one of the binding partners of the immobilized biological or biochemical or synthetic recognition elements or to the biological or biochemical or synthetic recognition elements.

Characteristic for another embodiment of the method is, that a second or more luminescence labels of similar or different excitation wavelength as the first luminescence label and similar or different emission wavelength are used.

Thereby it is preferred, that wherein the second or more luminescence labels can be excited at the same wavelength as the first luminescence label, but emit at other wavelengths.

For other applications it is advantageous, if the excitation and emission spectra of the applied luminescent dyes do not overlap or overlap only partially.

Characteristic for one variant of the method is, that charge or optical energy transfer from a first luminescent dye, acting as a donor, to a second luminescent dye, acting as an acceptor, is used for the detection of the analyte.

For another possible embodiment of the method it is characteristic, that the extent of quenching of one or more luminescences is determined.

Characteristic for another embodiment of the method is, that besides determination of one or more luminescences, changes of the effective refractive index on the measurement areas are determined.

An improvement of the method is characterized, in that the one or more determinations of luminescences and/or determinations of light signals at the excitation wavelengths are performed polarization-selective.

It is preferred, that the one or more luminescences are measured at a polarization that is different from the one of the excitation light.

It is characteristic for a preferred embodiment of the method according to the invention, that the density of the recognition elements immobilized in discrete measurement areas for the detection of different analytes on different measurement areas is selected in such a way, that, upon determination of different analytes in a common array, the luminescence signals are of similar order of magnitude, i.e., that the related calibration curves for the analyte determinations to be performed simultaneously can be recorded without a change of the opto-electronic system adjustments.

Characteristic for an improvement of the method is, that arrays of measurement areas are arranged in segments of one or more measurement areas for analyte determination and of measurement areas for referencing, i.e. for the determination of physical parameters and/or of chemical differences between different applied samples. Thereby, one or more arrays can comprise segments of two or more measurement areas with biological or biochemical or synthetic recognition elements for analyte determination or for referencing, that are similar within said segment. However, a segment can also comprise several discrete measurement areas with recognition elements different from each other.

Characteristic for another possible variant of the method according to the invention is, that simultaneously on one or more segments of an array or on one or more arrays different analytes of a common group are determined, such as different cytokines upon their binding to different anti-cytokine antibodies.

For certain application, for example the determination of low-molecular compounds in immuno analytics or the detection of single-point mutations in nucleic acid analytics, a cross-reactivity with the (bio)chemically most similar compounds can hardly be avoided. For such applications, an embodiment of the kit according to the invention can be advantageous, wherein one or more measurement areas of a segment or of an array are provided for the same analyte, and wherein the related immobilized biological or biochemical recognition elements have different affinities for said analyte. Thereby it is convenient, if the recognition elements are selected in such a way that their affinities to different, but (bio)chemically rather similar analytes, change from recognition element to recognition element in a different, characteristic manner. Then the identity of the analyte can be determined from the totality of the signals from different measurement areas with different recognition elements for a single analyte, in a similar way like a finger print.

Characteristic for another possible variant is, that simultaneously different analytes of different groups, such as pharmaceutical drugs for the treatment of a disease and/or their metabolites and/or the indicator compounds for said disease like so-called "marker proteins", are determined on one or more segments of an array or on one or more arrays.

For example for the investigation of aspects of reproducibility it can be advantageous, if two or more identical measurement areas are provided for the determination of each analyte or for physical or chemical referencing within a segment or an array. Thereby, said identical measurement areas can be arranged in a continuous row or column or diagonal of an array or a segment of measurement areas.

For addressing other questions, for example for investigating systematic local differences of the excitation conditions, it can be advantageous, if said identical measurement areas are distributed statistically within an array or a segment of measurement areas.

Characteristic for one possible embodiment of the method according to the invention is, that the laterally resolved referencing of the excitation light intensity available in the measurement areas comprises the simultaneous or sequential generation of an image of the light emanating from the sensor platform at the excitation wavelength. Thereby it is preferred, that the generation of an image of the excitation light emanating from the sensor platform is performed using the same optical path as for the collection of the luminescences emanating from the measurement areas.

As another possible embodiment of the method, the laterally resolved referencing of the excitation light intensity available in the measurement areas comprises the simultaneous or sequential generation of an image of the light emanating from the sensor platform at the luminescence wavelength.

Characteristic for another embodiment is, that the means for the laterally resolved referencing of the excitation light intensity available in the measurement areas comprise the simultaneous or sequential generation of an image of the light emanating from the sensor platform at another excitation wavelength as used for excitation of a luminescence. Thereby it is preferred, that the excitation wavelength for the locally resolved referencing is selected in such a way that molecules capable of luminescence and applied during the assay for the detection of one or more analytes or for purposes of referencing or of calibration have no absorption or an absorption as low as possible at said wavelength, so that effects of "photochemical bleaching" can be avoided or minimized.

It is preferred, that the local resolution of the image for referencing the excitation light emanating from the sensor platform is below 100 µm, preferably below 20 µm.

A further subject of the method according to the invention is, that the laterally resolved referencing of the excitation light intensity available in the measurement areas is performed by means of "luminescence marker spots", i.e., of the luminescence intensity from measurement areas with pre-immobilized luminescently labeled molecules (i.e., which molecules have been deposited in these measurement areas already before supply of a sample).

Thereby, it is preferred, that the "luminescence marker spots" are provided as a screen spreading over the whole sensor platform.

An improvement of the method according to the invention is, that wherein the density of the luminescently labeled molecules is selected, upon mixing with similar, but non-labeled molecules for immobilization, in such a way that the luminescence intensity from the regions of the "luminescence marker spots" is of similar order of magnitude as the luminescence intensity from the measurement areas dedicated for an analyte determination.

Characteristic for a preferred embodiment of the method is, that the density and the concentration of the luminescently labeled molecules within a "luminescence marker spot" is uniform within an array, preferably uniform on the whole sensor platform.

It is a known fact, that a molecule capable of luminescence can be exposed to only a limited number of cycles of excitation by an external excitation light, followed by its deactivation upon the emitted luminescence, before it is photochemically destroyed, i.e. is transformed into another molecule, which, in general, is no more capable of luminescence. This process is generally called "photobleaching". The number of possible cycles of activation and deactivation is an average value characteristic for a certain type of molecule (comparable with the half-life period of a radioactive compound). In order to guarantee the effectiveness of referencing in a method according to the invention to an extent as large as possible, it is preferred that a decrease of the signals from the "luminescence marker spots", for example to be caused by "photobleaching" during adjustments of the optical system, is minimized.

It is also preferred, that the laterally resolved referencing of the excitation light intensity available in the measurement areas comprises the determination of an average of multiple locally resolved reference signals.

The supply of the one or more samples and the reagents to be applied in the determination method can be performed sequentially, in several steps. It is preferred, that the one or more samples are pre-incubated with a mixture of the various tracer reagents for the determination of the analytes to be determined in said samples, and wherein these mixtures are then brought into contact with the corresponding dedicated arrays in a single supply step.

Characteristic for a preferred embodiment of the method according to the invention is, that the concentration of the tracer reagents, such as secondary tracer antibodies and/or luminescence labels and optional additional luminescently labeled tracer reagents in a sandwich immunoassay, is selected in such a way that the luminescence signals are of similar order of magnitude, i.e., that, upon determination of different analytes in a common array, the related calibration curves for the analyte determinations to be performed simultaneously can be recorded without a change of the optoelectronic system adjustments.

A further subject of an embodiment of the method according to the invention is, that the calibration of one or more luminescences generated in the near-field of layer (a) as a consequence of the binding of one or more analytes or of the specific interaction with one or more analytes comprises the application of one or more calibration solutions with known concentrations of said analytes to be determined on the same or on other measurement areas or segments of measurement areas or arrays of measurement areas on a sensor platform, on which the one or more samples to be analyzed are applied at the same or at a different supply step.

Characteristic for a special embodiment of the method is, that the calibration of one or more luminescences generated in the near-field of layer (a) as a consequence of the binding of one or more analytes or of the specific interaction with one or more analytes comprises the addition of an optionally additional analyte at a known concentration to one or more samples to be analyzed, for analysis on one or more dedicated measurement areas of the sensor platform.

Characteristic for another preferred embodiment of the method is, that the calibration of one or more luminescences generated in the near-field of layer (a) as a consequence of the binding of one or more analytes or of the specific interaction with one or more analytes comprises the comparison of the luminescence intensities after application of an unknown sample and of a control sample, such as the comparison after application of a "wild type" DNA sample and of a "mutant DNA" sample. Thereby it is possible, that the unknown sample and the control sample are applied on different arrays.

Characteristic for another variant of this method is, that the unknown sample and the control sample are applied sequentially on the same array. In general, it is necessary for this embodiment of to perform a regeneration step between the supply of the unknown sample and the control sample, i.e., the dissociation of recognition element—analyte complexes, formed after supply of the first sample, followed by the removal of the dissociated analyte molecules from the sample compartments, before the supply of the second sample can be performed. In a similar way, also several samples can be analyzed for their analytes on an array of measurement areas in a sequential way.

Characteristic for another embodiment of the method is, that the unknown sample and the control sample are mixed, and wherein the mixture is then applied on one or more arrays of the sensor platform.

Characteristic for an improvement of the method according to the invention is, that the detection of the analytes to be determined in the unknown and the control sample is performed using luminescence labels with different excitation and/or luminescence wavelength for the unknown and for the control sample.

For example, it is preferred that the determination of analytes of different groups is performed using two or more luminescence labels with different excitation and/or luminescence wavelengths.

The use of several different luminescence labels can also be advantageous for the determination of different analytes of a common group. Characteristic for another preferred embodiment of the method according to the invention is, that, for example for the determination of the cross-reactivity between analytes of a common group, such as cytokines, the determination is performed using two or more luminescence labels with different excitation and/or luminescence wavelengths.

As described above, the kit according to the invention, with the large number of measurement areas on a single sensor platform, provides the possibility of a simplified type of calibration for the qualitative and/or quantitative determination of one or more analytes on one or more arrays. In the best case, the application of only a single calibration solution is required for this new, inventive type of calibration of the signals from a sensor platform. Therefore it is preferred for this improvement of the method according to the invention, that in one or more arrays always several measurement areas with biological or biochemical or synthetic recognition elements immobilized therein at a different, controlled density are provided, for the determination of an analyte that is common for these measurement areas. It is characteristic for this improvement of the method, that a calibration curve for an analyte can already be established upon application of a single calibration solution to an array comprising biological or biochemical or synthetic recognition elements for said analyte, immobilized in different measurement areas of that array at a sufficiently large "variation" of different controlled density, the concentration dependence of the signals indicative for the binding between said analyte and said biological or biochemical or synthetic recognition elements being known.

Characteristic for a further preferred variant of the method according to the invention is, that the calibration of one or more luminescences generated in the near-field of layer (a) as a consequence of the binding of one or more analytes or of the specific interaction with one or more analytes comprises the determination of the luminescence intensity caused by the presence of one or more analytes in a series of samples at an essentially constant concentration. Especially in DNA-analytics, for example for the comparison of so-called "wild-type" and "mutant" samples, so-called house-keeping genes are known, the content of which is essentially constant in a series of samples of different origin (tissue, type of organism, etc.). Similarly, in immuno analytics certain immuno globulins are known, the concentration of which does vary only little between samples from a common type of organism.

Part of the invention is a method according to any of the embodiments described above for the simultaneous or sequential, quantitative or qualitative determination of one or more analytes of the group comprising antibodies or antigens, receptors or ligands, chelators or "histidin-tag components", oligonucleotides, DNA or RNA strands, DNA or RNA analogues, enzymes, enzyme cofactors or inhibitors, lectins and carbohydrates.

Characteristic for possible embodiments of the method is also, that the samples to be examined are naturally occurring body fluids, such as blood, serum, plasm, lymph or urine or egg yolk or optically turbid liquids or tissue fluids or surface water or soil or plant extracts or bio- or process broths, or are taken from biological tissue fractions or from cell cultures or cell extracts.

A further subject of the invention is the use of a kit according to the invention and/or of an analytical system according to the invention and/or of a method according to the invention for the quantitative or qualitative analyses for the determination of chemical, biochemical or biological analytes in screening methods in pharmaceutical research, combinatorial chemistry, clinical and pre-clinical development, for real-time binding studies and for the determination of kinetic parameters in affinity screening and in research, for qualitative and quantitative analyte determinations, especially for DNA- and RNA analytics, for generation of toxicity studies and for the determination of gene and protein expression profiles, and for the determination of antibodies, antigens, pathogens or bacteria in pharmaceutical product development and research, human and veterinary diagnostics, agrochemical product development and research, for symptomatic and pre-symptomatic plant diagnostics, for patient stratification in pharmaceutical product development and for the therapeutic drug selection, for the determination of pathogens, nocuous agents and germs, especially of salmonella, prions and bacteria, in food and environmental analytics.

The invention will be explained further in the following examples, without a restriction of the scope of the invention.

EXAMPLES OF APPLICATIONS

Example 1

Figure 1:
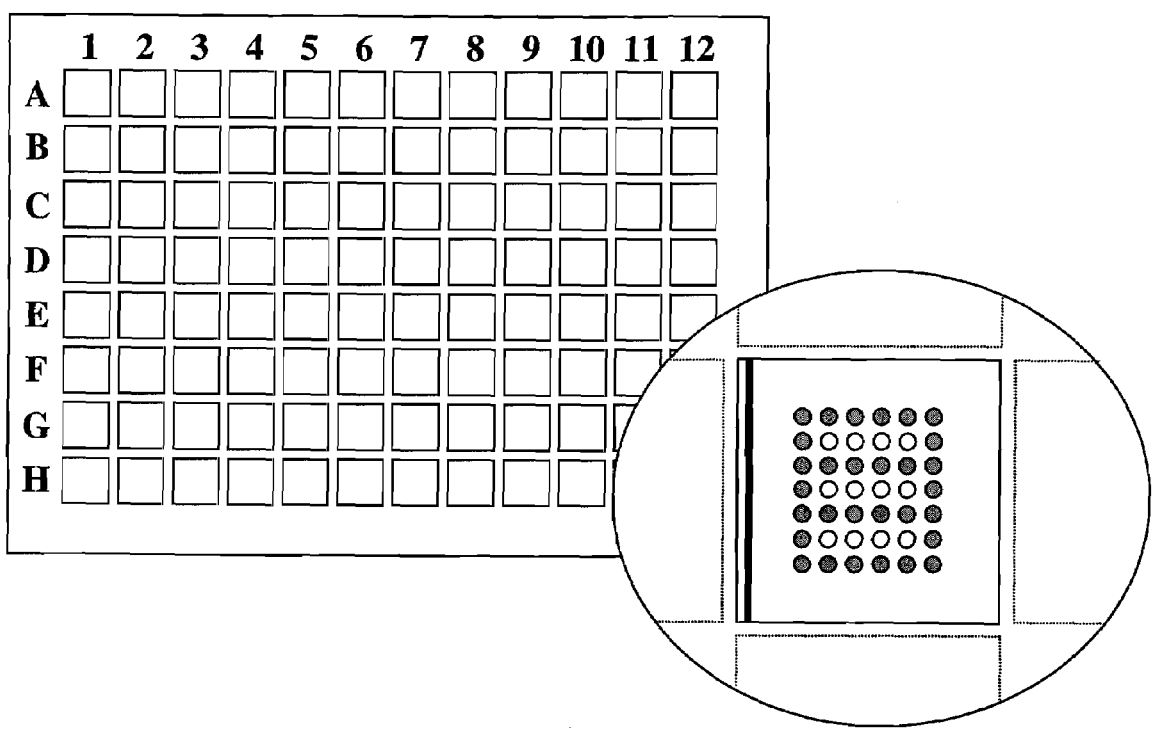
FIG. 1 illustrates different recognition elements being arranged in a plurality of rows of a replica of identical measurement areas, where each row is arranged parallel to the direction of propagation of excitation light in a waveguide according to an embodiment of the present invention.

Kit for the Simultaneous Quantitative Determination of Multiple Cytokine Marker Proteins in One or Multiple Samples for Analysis a) The major component of a kit according to the invention is a rectangular sensor platform with the external dimensions 113.5 mm×75.0 mm×0.7 mm thickness, combined with an 11 mm thick polycarbonate (PC) layer, which is inked in black for suppression of effects due to scattered light. Open quadratic recesses (wells) of 7 mm×7 mm lateral side each, at a center-to-center distance of 9 mm, have been provided in the PC layer, which are used as sample compartments for receiving sample volumes to be analyzed (10-100 μl). The recesses are arranged in 12 columns and 8 rows in one plane, so that the combination of the sensor platform with the PC structure comprises 96 sample compartments in total.

The substrate material of the sensor platform (optically transparent layer (b)) consists of AF 45 glass (refractive index n=1.52 at 633 nm). Continuous surface relief gratings (over the whole length of 75 mm of the sensor platform) are generated in the substrate at a distance of 9 mm, with a width of 0.5 mm (in direction of propagation of the excitation light to be in-coupled into the layer (a) of the sensor platform by means of the grating structure). These gratings have a period of 360 nm and a depth of 12 nm, with orientation of the grating lines in parallel to the columns of the wells, The waveguiding, optically transparent layer (a) of $Ta_2O_5$ on the optically transparent layer (b) has a refractive index of 2.11 at 633 nm (layer thickness 150 nm). Due to the deposition process, the grating structure of the optically transparent layer (b) is transferred into the surface of the deposited layer (a) almost at to scale 1:1.

Before combination with the polycarbonate structure, the surface of the sensor platform is cleaned by wet chemical methods, first several times with iso-propanol, then with concentrated sulfuric acid containing 2.5% ammonium peroxodisulfate. Then a mono-molecular layer (monolayer) of mono-octadecylphosphate is deposited as an adhesion-promoting layer on the hydrophilic waveguide surface by means of self-assembly. This surface modification leads to a hydrophobic surface (contact angle about 110° against water). The method of surface modification has been described in more detail in the literature (D. Brovelli et al., Langmuir 15 (1999) 4324-4327).

96 identical arrays (arranged in 12 columns×8 rows) of 42 measurement areas (spots) each (in an arrangement of 7 columns×6 rows for each array) are generated on the hydrophobic surface of the sensor platform provided with the adhesion-promoting layer, using an inkjet plotter. Model NPIC (GeSiM, Grosserkmannsdorf, DE).

The recognition elements for the determination of different human interleukins, as analytes of the group of cytokines (recognition elements: monoclonal mouse antibodies anti-hIL-2, anti-hIL-4, and anti-hIL-6) are reconstituted at a concentration between 300 and 1000 μg/ml in a 10% phosphate-buffered salt solution (PBS, pH 7.4). Then the antibody solutions are diluted to a different extent in 10% PBS (pH 7.4), which extent is determined by the affinity of the actual antibody to the corresponding antigen. The adequate concentrations (100 μg/ml for anti-hIL-2 and anti-hIL-6; 50 μg/ml for anti-hIL-4 antibodies) have been determined before in single-analyte interleukin immunoassays. Thus it shall be achieved that the dynamic range of the signal intensities to be expected in an assay for the simultaneous determination of all three interleukins on one array is of similar order of magnitude. It is demonstrated for this aspect of the example, that it is possible that the dynamic range of the signal intensities to be expected in an assay for the simultaneous determination of a multitude of different analytes, is within the same order of magnitude within one array, upon adequate choice of the immobilization density of different recognition elements with different affinities for the corresponding analytes to be determined in discrete measurement areas.

After deposition of the antibodies on the adhesion-promoting layers, it (the sensor platform) is incubated for 15 minutes in a saturated water vapor atmosphere. Then that hydrophobic surface of the sensor platform not covered with proteins is saturated with a solution of bovine serum albumin (BSA) in PBS (1 mg/ml, pH 7.4), containing an admixture of 0.05% Tween 20, for minimization of nonspecific binding of tracer antibodies in the later determination method. Then the sensor platform is washed with water and dried with nitrogen.

The diameter of the spots, arranged at a center-to-center distance of 500 µm, is about 220 µm. Each single array comprises three different types of recognition elements (for recognition of hIL-2, hIL-4, and hIL-6) and "luminescence marker spots" with bovine serum albumin fluorescently labeled with Cy5 (Cy5-BSA). Thereby, the immobilization density is selected in such a way, that the luminescence intensity of these "luminescence marker spots" is also within the dynamic range of the changes of signal intensities to be expected in the course of the interleukin assay. For the actual example, a 25-picomolar solution of Cy5-BSA, at a labeling rate of 10 Cy5 molecules per BSA molecule, is determined as the optimum concentration of Cy5-BSA in the immobilization solution. In addition it is found, that the application of a mixture of fluorescently labeled and of non-labeled BSA molecules as immobilization solution is significantly better suited for achieving a homogeneous distribution of the fluorescently labeled BSA molecules in the "luminescence marker spots" than the application of a solution containing only the fluorescently labeled protein, at a correspondingly lower protein concentration. An immobilization solution with a concentration of 25 µg/ml non-labeled BSA in 10% PBS (pH 7.4) and the content of 25 pM Cy5-BSA already mentioned is found to be optimum. The reproducibility of the deposition of the "luminescence marker spots" was investigated using sensor platforms produced in the same way as described above, but were measured using a regular commercial scanner (Genetic Microsystems 418 Array Scanner). Thereby, a variation of the luminescence intensity, integrated always for a "luminescence marker spot", of only 3%-4% was determined.

The different recognition elements are arranged in three rows of four replica of identical measurement areas (spots) each, as shown in FIG. 1, wherein these rows are arranged in parallel to the direction of propagation of the excitation light in the waveguide, in order to obtain already statistical information about the assay reproducibility from each individual measurement per sample to be supplied. The "luminescence marker spots" are arranged in four rows of four spots each, in parallel to the rows of spots with recognition elements. The "luminescence marker spots" are used for referencing the available excitation light adjacent to the measurement areas for analyte detection. Their arrangement in rows in parallel to the direction of propagation of the excitation light to be in-coupled into and to be guided in the layer (a) is also used for the determination of the damping (attenuation) of the excitation light in the direction of propagation. Additionally two columns of "luminescence marker spots" with seven replica each are provided at the beginning and at the end of an array. With respect to the direction of propagation of the in-coupled and guided excitation light. They are used for determination of the homogeneity of the available excitation light intensity in parallel to the lines of the in-coupling grating.

Example 2

Analytical System with a Kit According to the Invention

The sensor platform is mounted on a computer-controlled adjustment unit allowing for translation in parallel and perpendicular to the grating lines and for rotation around an axis of rotation in parallel to the grating lines of the sensor platform. Directly after the laser used as the excitation light source is located a shutter in the optical path, which is used to block the light path when no measurement data shall be collected. Neutral density filters or polarizators can be inserted additionally into the light path at this position or also at other positions in the further path of the excitation light towards the sensor platform, in order to vary the excitation light intensity step-wise or continuously.

The excitation light beam of a helium neon laser at 632.8 nm (Melles-Griot 05-LHP-901, 1.1 mW) is expanded in one dimension by a cylindrical lens and directed though a slit-type diaphragm (opening 0.5 mm×7 mm), in order to generate a light bundle of almost rectangular cross-section and of almost homogeneous cross-sectional intensity. Thereby, the polarization of the laser light is adjusted in parallel to the grating lines of the sensor platform, for excitation of the $TE_0$-mode at in-coupling conditions. The excitation light is directed onto the in-coupling grating within one of the 96 sample compartments from the back side of the sensor platform, i.e. through the optically transparent layer (b), wherein the in-coupling grating for an array of measurement areas within a sample compartment is located, under the conditions of this example, always at the left edge of the square-type well. The angle between the sensor platform and the irradiated excitation light bundle is adjusted by rotation around the axis described above, for maximum in-coupling into the optically transparent layer (a). For the described parameters of the sensor platform the resonance angle for in-coupling in air is about 2.6°.

A CCD camera (Ultra Pix 0401E, Astrocam, Cambridge, UK) with Peltier cooling (operation temperature −30° C.), with a Kodak CCD chip KAF 0401 E-1 is used as locally resolving detector. Signal collection and focusing onto the CCD chip is performed using a Computar tandem objective (f=50 mm, 1:1.3). Mounted on a filter exchanger, two interference filters (Omega, Brattleborough, Vt.) with central transmission wavelength of 680 nm and 40 nm bandwidth, and either a neutral density filter (for transmission of the attenuated, scattered excitation light and of the much weaker luminescence light from the measurement areas) or a neutral density filter combined with an interference filter (for transmission of the attenuated excitation light scattered at the measurement areas) are located between the two halves of the tandem objective. The signals at the excitation and the luminescence wavelength can be measured in turns. Data analysis is performed using commercially available image analysis software (ImagePro Plus).

Example 3

Detection Method Using a Kit According to the Invention

For the specific recognition of the interleukins to be determined the format of a sandwich assay is chosen.

Sample Preparation:

Eight mixed calibration solutions of the interleukins (hIL-2. hIL-4, and hIL-6) to be determined quantitatively, each containing all three interleukins at the same concentration (00, 10, 30, 70, 150, 300, 600, 1000 pg/ml), are produced, each in 50 µl PBS (pH 7.4) containing 0.1% BSA and 0.05% Tween 20. These calibration solutions are dedicated for the simultaneous generation of calibration curves for all three analytes upon application on the corresponding dedicated arrays on the sensor platform.

The calibration solutions, as well as the samples with unknown concentrations of the three interleukins to be determined as the analytes, are then each mixed with 50 µl of a solution containing a mixture of three secondary, poly-clonal tracer antibodies ($5 \times 10^{-10}$ M biotinylated anti-hIL-2 antibody, $10^{-10}$ M biotinylated anti-hIL-4 antibody, and $10^{-10}$ M biotinylated anti-hIL-6 antibody in PBS (pH 7.4), with 0.1% BSA and 0.05% Tween 20). These mixtures of 100 µl volume each are then each mixed with a solution of Cy5-streptavidin ($5 \times 10^{-10}$ M, Amersham-Pharmacia) in PBS (pH 7.4), containing 0.1% BSA and 0.05% Tween 20. The concentrations of the three different tracer antibodies reported above are selected in such a way, that the expected changes of fluorescence intensities, resulting from the specific binding of the antigen—secondary antibody—complexes to their immobilized mono-clonal recognition antibodies as recognition elements in the discrete measurement areas, are of similar order of magnitude, i.e. that the corresponding calibration curves can be recorded without a change of the opto-electronic system adjustments.

It is demonstrated on this aspect of the example, that it is possible upon adequate choice of the concentrations of the tracer reagents, that the expected fluorescence intensities, resulting from their specific binding to the corresponding recognition elements immobilized in discrete measurement areas, are of the same order of magnitude for all analytes to be determined simultaneously in a single assay, i.e. that the corresponding calibration curves can be recorded without a change of the opto-electronic system adjustments.

Then the produced mixed solutions are incubated for one hour in the dark, before the incubates (100 µl each) are filled into the sample compartments. Thereby, the calibration solutions are filled into the sample compartments of the arrays A1 to H1 (microtiter plate format, see FIG. 1) at increasing concentration, whereas the 88 samples to be analyzed, containing unknown concentrations of the three interleukins as analytes, are filled into the other sample compartments A2 to H12. After a further incubation in the dark for two hours, the arrays are measured.

Read-out of the Arrays:

For the read-out of the fluorescence signals from the measurement areas of the different arrays, the sensor platform with the sample compartments thereon and containing the solutions, is mounted on the adjustment unit described above, which is located within the analytical system. For determination of the luminescence signals from each array, the sensor platform is adjusted for maximum in-coupling of the excitation light by means of the grating structure dedicated for the array to be measured, which adjustment is controlled with positioning the filter exchanger for the excitation wavelength. Then the intensity of the fluorescence light from the measurement areas (spots) is measured with position of the filter exchanger for the luminescence wavelength. The read-out of the arrays in the further sample compartments is performed sequentially, upon translation of the sensor platform to the next position for read-out of the luminescence signals from the next sample compartment.

Data Analysis and Referencing:

The image analysis is performed using a commercially available image analysis software (ImagePro Plus). Thereby, the integrated fluorescence intensity is determined for each spot for each array. Thus, always four integrated values of fluorescence intensities per array are obtained for the three interleukins, from which four values are then calculated, for statistical purposes, the average values and the standard deviations.

Additionally, the two Cy5-BSA reference spots ("luminescence marker spots"), of the first column of the array before and of the last column of the array behind the corresponding row of always four measurement areas for the interleukin determination, are analyzed and averaged in a similar way. This averaged reference value is always used for the correction of the luminescence signals from the measurement areas for analyte determination located in the same row.

Correspondingly, the average values for the Cy5-BSA reference spots before and behind the interleukin measurement areas in the same row are determined for each array. Then, another average value is calculated from these in total 96 determined reference values for each of the three analytes. Then the individual correction factor for the measurement values for analyte determination in an array is determined as the ratio between the local reference value and the average value just described. The local differences of the available excitation light intensity on a common sensor platform are compensated by multiplication with this correction factor.

For a comparison of the results with different sensor platforms (in case of the present example three sensor platforms), the luminescence intensities corrected by the method described above are set to the normalized value of 1 for an interleukin concentration of 0 pg/ml.

Figure 2:
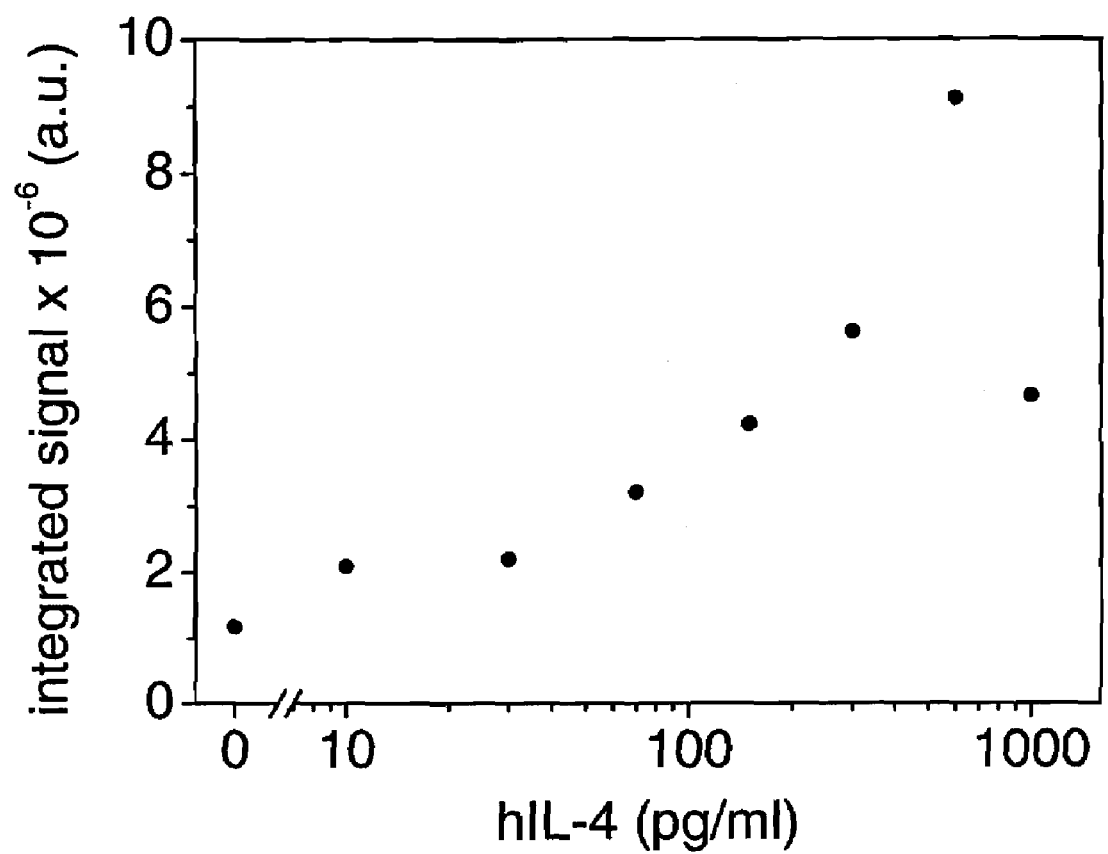
FIG. 2 depicts uncorrected raw data obtained for the determination of interleukin 4 for the calibration of a multi-analyte immunoassay, where the integrated values of the fluorescent intensities are depicted as a function of the human interleukin 4 concentration.
Figure 3:
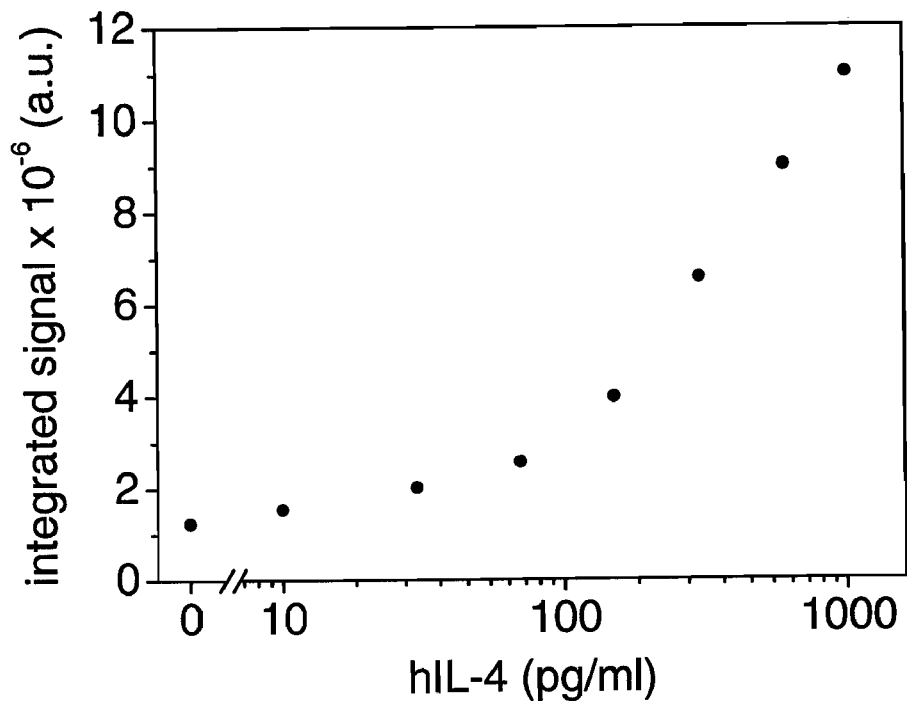
FIG. 3 depicts calibration data obtained by an average calculation method for the calibration of a multi-analyte immunoassay, where the integrated values of the fluorescent intensities are depicted as a function of the human interleukin 4 concentration.

As an example, the uncorrected raw data obtained for the determination of interleukin 4 and dedicated for the calibration of this multi-analyte immunoassay, are shown in FIG. 2, where the integrated values of the fluorescence intensities are depicted as a function of the hIL-4 concentration. FIG. 3 shows the calibration data obtained by the method of average calculation described above.

Figure 4:
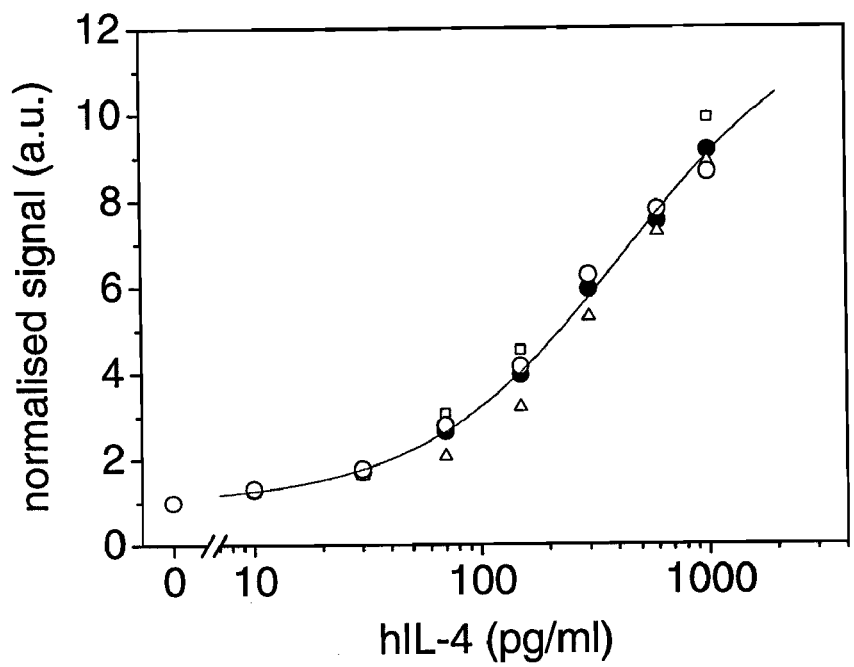
FIG. 4 is graph showing a Hill function fitted to corrected calibration data.
Figure 5:
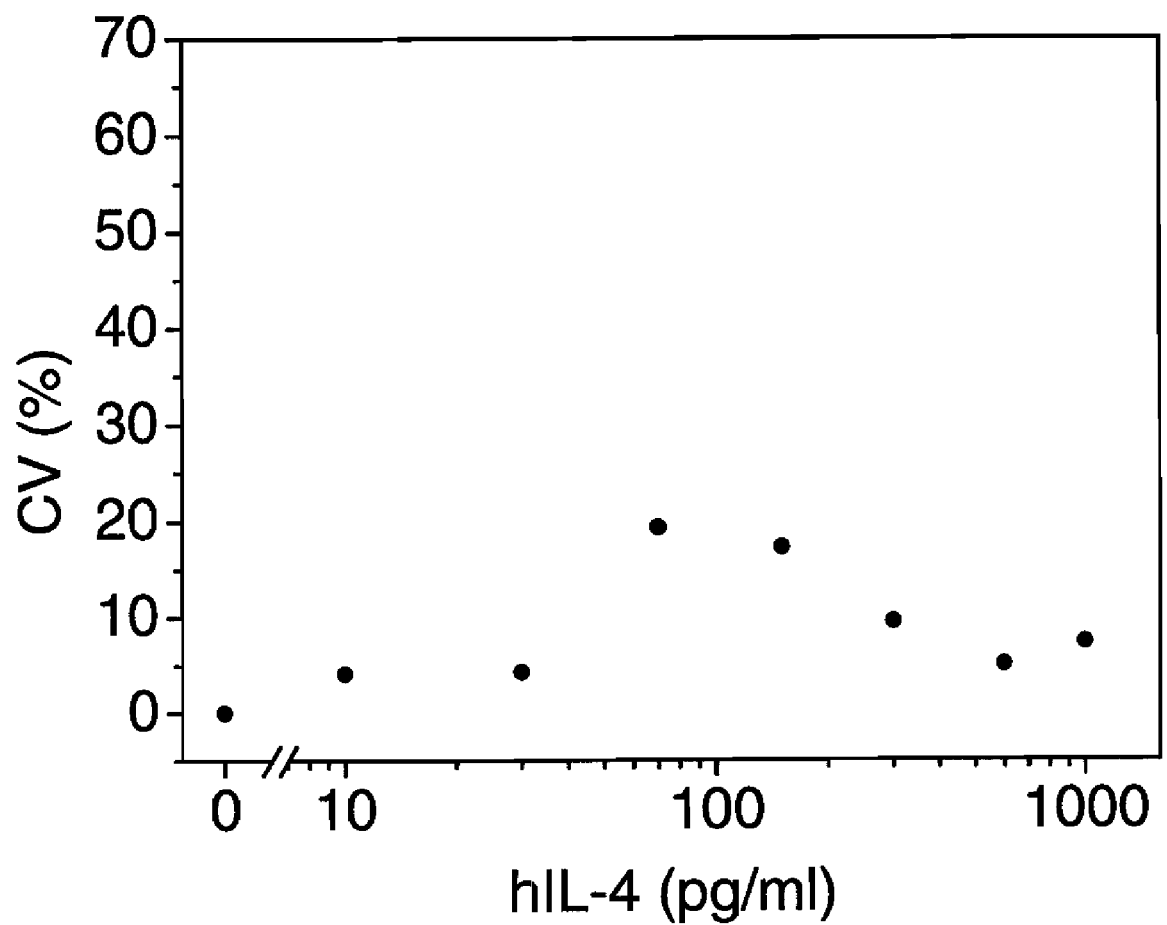
FIG. 5 is a graph showing experimental results obtained from a complete multi-analyte immunoassay performed on a single sensor platform according to an embodiment of the present invention.

The continuous curve in FIG. 4 represents the Hill function fitted to these corrected data. The empty symbols represent the corrected calibration signals determined with three different sensor platforms. The filled circles represent the average values determined therefrom, for the different hIL-4 concentrations. Thus it is obtained as a surprising total result, that a variability of the signals of only 5% to 20%, even when different sensor platforms are compared (FIG. 5), was achieved by means of a kit according to the invention and the determination method based thereon, i.e. in a complete multi-analyte immunoassay performed always on a single sensor platform, upon generation of a complete calibration curve on each platform.

The invention claimed is:

1. A method for the simultaneous qualitative and/or quantitative determination of a multitude of analytes comprising:
   bringing one or more liquid samples to be analyzed for the analytes into contact with measurement areas of a sensor platform,
   the sensor platform comprising
   an optical thin film waveguide with a first layer, that is transparent at least at one excitation wavelength, on a second layer that has a lower refractive index than the first layer and is also transparent at least at the excitation wavelength, and at least one grating structure modulated in the first layer for in-coupling of the excitation light into the first layer;
   at least one array of biological or biochemical or synthetic recognition elements immobilized in measurement areas for detection of different analytes by specific recognition and/or binding of said analytes and/or by specific interaction with said analytes,
   means for laterally resolved referencing of the excitation light intensity available in the measurement areas and, optionally,
   means for the calibration of one or more luminescences generated in a near field of the first layer, the measurement areas for detection of different analytes being usable for detection of analytes to be determined and/or as means for calibration purposes;

irradiating an excitation light towards the measurement areas;

detecting an emission light from the measurement areas;

referencing the excitation light intensity available in the measurement areas in a locally resolved way by means of correcting the emission light intensity from measurement areas for detection of different analytes using the means for laterally resolved referencing of the excitation light intensity available in the measurement areas;

calibrating one or more luminescences generated in a near-field of the first layer from the measurement areas that result from the binding of one or more analytes to biological or biochemical or synthetic recognition elements immobilized in the measurement areas or from interaction between the analytes and the immobilized recognition elements using the measurement areas for detection of different analytes as means for calibration purposes to establish a calibration curve on each platform; and comparing the emission light intensity from measurement areas for detection of analytes in the sample to be analyzed to the calibration curve for qualitative and/or quantitative determination of the analyte.

2. A method according to claim 1, wherein the excitation light is in-coupled into the optically transparent first layer towards the measurement areas by the grating structure.

3. A method according to claim 1, wherein the sensor platform comprises even, non-modulated regions of the first layer, which are arranged in the direction of propagation of an excitation light in-coupled into the first layer by the grating structure and guided in the first layer.

4. A method according to claim 1, wherein isotropically emitted luminescence or luminescence that is in-coupled into the optically transparent first layer and out-coupled by the grating structure, or luminescence comprising both isotropically emitted luminescence or luminescence that is in-coupled into the optically transparent first layer and out-coupled by the grating structure, is measured simultaneously.

5. A method according to claim 1, wherein, for the generation of said luminescence, a luminescent dye or a luminescent nano-particle is used as a luminescence label, which can be excited and emits at a wavelength between 300 nm and 1100 nm.

6. A method according to claim 5, wherein the luminescence label is bound to the analyte or, in a competitive assay, to an analyte analogue or, in a multi-step assay, to one of the binding partners of the immobilized biological or biochemical or synthetic recognition elements or to the biological or biochemical or synthetic recognition elements.

7. A method according to claim 5, wherein a second or more luminescence labels of similar or different excitation wavelength as the first luminescence label and similar or different emission wavelength are used.

8. A method according to claim 7, wherein the second or more luminescence labels can be excited at the same wavelength as the first luminescence label, but emit at other wavelengths.

9. A method according to claim 7, wherein the excitation and emission spectra of the applied luminescent dyes do not overlap or overlap only partially.

10. A method according to claim 7, wherein charge or optical energy transfer from a first luminescent dye, acting as a donor, to a second luminescent dye, acting as an acceptor, is used for the detection of the analyte.

11. A method according to claim 1, wherein one or more determinations of luminescences and/or determinations of light signals at the excitation wavelengths are performed polarization-selective, wherein preferably the one or more luminescences are measured at a polarization that is different from the one of the excitation light.

12. A method according to claim 1, wherein, besides determination of one or more luminescences, changes of the effective refractive index on the measurement areas are determined.

13. A method according to claim 1, wherein the density of the recognition elements immobilized in discrete measurement areas for the detection of different analytes on different measurement areas is selected in such a way, that, upon determination of different analytes in a common array, the luminescence signals are of similar order of magnitude, so that the related calibration curves for the analyte determinations to be performed simultaneously can be recorded without a change of the opto-electronic system adjustments.

14. A method according to claim 1, wherein arrays of measurement areas are arranged in segments of one or more measurement areas for analyte determination and of measurement areas for referencing, for the determination of physical parameters and/or of chemical differences between different applied samples.

15. A method according to claim 1, wherein one or more arrays comprise segments of two or more measurement areas with biological or biochemical or synthetic recognition elements for analyte determination or for referencing, that are similar within said segment.

16. A method according to claim 1, wherein one or more measurement areas of a segment or of an array are provided for the same analyte, and wherein the related immobilized biological or biochemical recognition elements have different affinities for said analyte.

17. A method according to claim 1, wherein simultaneously on one or more segments of an array or on one or more arrays different analytes of a common group are determined.

18. A method according to claim 1, wherein simultaneously different analytes of different groups are determined on one or more segments of an array or on one or more arrays.

19. A method according to claim 1, wherein two or more identical measurement areas are provided for the determination of each analyte or for physical or chemical referencing within a segment or an array.

20. A method according to claim 19, wherein said identical measurement areas are arranged in a continuous row or column or diagonal of an array or a segment of measurement areas.

21. A method according to claim 19, wherein said identical measurement areas are distributed statistically within an array or a segment of measurement areas.

22. A method according to claim 1, wherein the laterally resolved referencing of the excitation light intensity available in the measurement areas comprises the simultaneous or sequential generation of an image of the light emanating from the sensor platform at the excitation wavelength.

23. A method according to claim 1, wherein said referencing of the excitation light intensity available in the measurement areas comprises the simultaneous or sequential generation of an image of the light emanating from the sensor platform at another excitation wavelength as used for excitation of a luminescence.

24. A method according to claim 23, wherein the excitation wavelength for said referencing is selected in such a way that molecules capable of luminescence and applied during the assay for the detection of one or more analytes or for purposes of referencing or of calibration have no absorption or absorption as low as possible at said wavelength.

25. A method according to claim 22, wherein the generation of an image of the excitation light emanating from the sensor platform is performed using the same optical path as for the collection of the luminescences emanating from the measurement areas.

26. A method according to claim 1, wherein said referencing of the excitation light intensity available in the measurement areas comprises the simultaneous or sequential generation of an image of the light emanating from the sensor platform at the luminescence wavelength.

27. A method according to claim 1, wherein the local resolution of the image for said referencing the excitation light emanating from the sensor platform is below 100 μm.

28. A method according to claim 1, wherein said referencing of the excitation light intensity available in the measurement areas is performed using luminescence marker spots comprising luminescence intensity from measurement areas with pre-immobilized luminescently labeled molecules which have been deposited in the measurement areas before supply of a sample.

29. A method according to claim 28, wherein the luminescence marker spots are provided as a net screen spreading over the whole sensor platform.

30. A method according to claim 1, wherein said referencing of the excitation light intensity available in the measurement areas comprises the determination of an average of multiple locally resolved reference signals.

* * * * *